United States Patent
Ben-Ur

(10) Patent No.: US 6,377,011 B1
(45) Date of Patent: Apr. 23, 2002

(54) FORCE FEEDBACK USER INTERFACE FOR MINIMALLY INVASIVE SURGICAL SIMULATOR AND TELEOPERATOR AND OTHER SIMILAR APPARATUS

(75) Inventor: Ela Ben-Ur, Somerville, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 09/491,788

(22) Filed: Jan. 26, 2000

(51) Int. Cl.$^7$ .............................. A61B 19/00; G05B 15/02
(52) U.S. Cl. .................. 318/566; 345/326; 345/184; 606/1; 901/34
(58) Field of Search ................................ 318/561, 565, 318/566, 568.1, 568.11, 625; 345/326, 339, 184; 600/101; 606/1; 901/30, 31, 32, 33, 34, 36, 38

(56) References Cited

U.S. PATENT DOCUMENTS

| | | | |
|---|---|---|---|
| 4,907,973 A | 3/1990 | Hon | 434/262 |
| 5,149,270 A | 9/1992 | McKeown | 434/262 |
| 5,403,191 A | 4/1995 | Tuason | 434/262 |

(List continued on next page.)

FOREIGN PATENT DOCUMENTS

WO    WO 99/50721    10/1999

OTHER PUBLICATIONS

Katherine S. Mangan, "Teaching Surgery Without a Patient," *The Chronicle of Higher Education*, vol. XLVI, No. 25, pp. A49–50, Feb. 25, 2000.

Surgical Technology Research, BioRobotics Lab, website, http://www.ee.washington.edu/BRL/device/surgical/, Dec. 23, 1999, "Force Reflective Endoscopic Grasper (FREG)," and "Instrumented Ednoscopic Grasper Surgeon/Endoscopic Tool Force/Torque Signatures in Minimally Invasive Surgery."

Hannaford et al., "Computerized Endoscopic Surgical Grasper," Proceedings: Medicine Meets Virtual Reality, San Diego, CA, Jan. 1998.

Immersion Impulse Engine, available from Immersion Corporation of San Jose, CA, 1998, photo enclosed.

A device developed by Ecole Polytechnique, the Bleuler Lab (Vollenweider, 1999), photo enclosed.

*Primary Examiner*—Bentsu Ro
(74) *Attorney, Agent, or Firm*—Steven J. Weissburg

(57) ABSTRACT

A handle module actuates handles of a user interface for various applications, including minimally invasive surgery ("MIS"). A modified MIS tool handle has two shafts that translate relative to each other upon relative motion of the handles. They also can rotate relative to each other. A housing engages both. The first is translationally fixed and rotatably free relative to the housing. An actuator actuates rotation of the first shaft. The second shaft is coupled to the housing such that it is rotationally fixed about and translatable along the axis of its elongation. The second shaft is fixed to a cartridge that is a linear capstan and translates relative to the housing, in response to relative translation of the shafts. A jaw action actuator is coupled to the cartridge through a cable drive, and can actuate the relative translation of the shafts, and thus, the handles. The jaw action actuator can actuate jaw action of a tool in a tool environment, either virtual, or actual. The first actuator can actuate rotation of the tool in a tool environment. The handle module can actuate both the jaw action of a jawed tool, as well as rotation around the long axis of the shafts. The actuation may also provide force feedback, for use as a simulator, or telerobotic master. A base mechanical interface can be added, that provides additional degrees of freedom, to enable simulation and force feedback that represent MIS insertion, pitch and yaw around the insertion point.

46 Claims, 9 Drawing Sheets

U.S. PATENT DOCUMENTS

| | | | |
|---|---|---|---|
| 5,623,582 A | * 4/1997 | Rosenberg | 395/99 |
| 5,625,576 A | 4/1997 | Massie et al. | 364/578 |
| 5,704,791 A | 1/1998 | Gillio | 434/262 |
| 5,766,016 A | 6/1998 | Sinclair et al. | 434/262 |
| 5,767,839 A | * 6/1998 | Rosenberg | 345/161 |
| 5,792,135 A | 8/1998 | Madhani et al. | 606/1 |
| 5,797,900 A | 8/1998 | Madhani et al. | 606/1 |
| 5,800,179 A | 9/1998 | Bailey | 434/262 |
| 5,807,377 A | 9/1998 | Madhani et al. | 606/1 |
| 5,828,197 A | 10/1998 | Martin et al. | 318/567 |

* cited by examiner

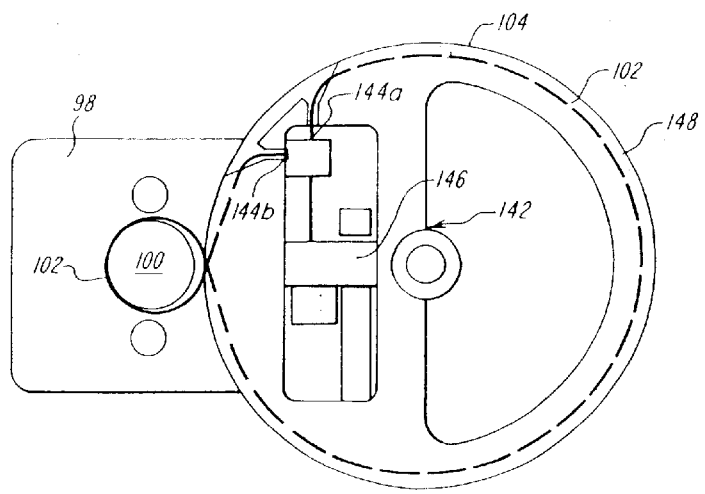
FIG. 15
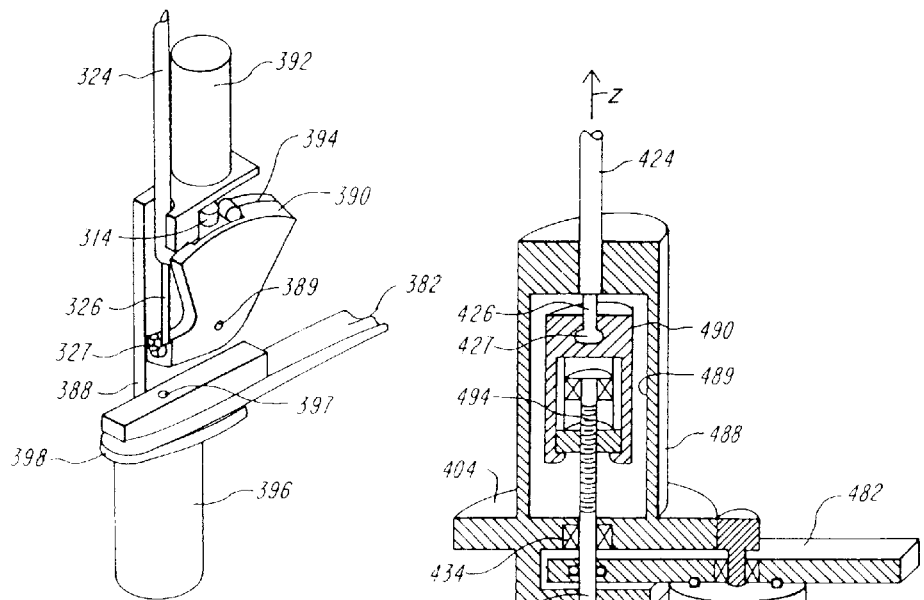
FIG. 16     FIG. 17

FORCE FEEDBACK USER INTERFACE FOR MINIMALLY INVASIVE SURGICAL SIMULATOR AND TELEOPERATOR AND OTHER SIMILAR APPARATUS

GOVERNMENT RIGHTS

The United States Government has certain rights in this invention pursuant to Contract DAMD17-99-2-9001, Sponsored by the U.S. Army Medical Research Acquisition Activity.

This material is based upon work supported under a National Science Foundation Graduate Fellowship. Any opinions, findings, conclusions or recommendations expressed in this publication are those of the author and do not necessarily reflect the views of the National Science Foundation.

BACKGROUND

Minimally invasive surgery techniques reduce the amount of extraneous tissue that are damaged during diagnostic or surgical procedures, thereby reducing patient recovery time, discomfort, and deleterious side effects, such as infection. Millions of the surgeries performed each year in the United States can be performed in a minimally invasive manner. However, far fewer of the surgeries performed currently use these techniques, due to limitations in minimally invasive surgical instruments and techniques and the additional training required to master them.

Advances in MIS technology could have a dramatic impact. The average length of a hospital stay for a standard surgery may be double that for the equivalent minimally invasive surgery. Thus, an increase of use of minimally invasive techniques could save many millions of hospital days and attendant costs alone. Patient recovery times, patient discomfort, surgical side effects, and time away from work are also reduced with minimally invasive surgery.

Endoscopy, a variety of MIS, generally refers to inserting tools into the body through natural orifices. Laparoscopy, another variety of MIS, refers to inserting tools through tiny incisions with sealed ports. In standard laparoscopic surgery, as shown schematically with reference to FIG. 1, a patient's abdomen is insufflated with gas, and cannula sleeves 510 are passed through small (approximately ½ inch (1 cm.)) incisions in the body wall 512 to provide entry ports for laparoscopic surgical instruments 514. The cannula holes may be created by a sharp pointed trocar, which may be equipped with an integral cannula. The following discussions are generally cast in terms of laparoscopy. However, the general principles apply to endoscopy also, and to most MIS.

The MIS instruments generally include a scope (endoscope or laparoscope), for viewing the surgical field, and working tools, such as blunt probes, dissectors, clamps, graspers, scissors, staplers, and needle holders. The working tools are similar to those used in conventional (open) surgery, except that, as shown in FIG. 1, the working end 516 of each tool is separated from its handle end 518 by an approximately 12-inch (30 cm) long extension tube 520. The view is typically displayed on a monitor.

To perform MIS procedures, the surgeon passes instruments through the cannula 510 and manipulates them inside the body by sliding them in and out through the cannula, along the z axis, as shown, rotating them in the cannula around the z axis, levering (i.e., pivoting around the x and y axes, as shown) the instruments in the body wall 512 and operating end effectors (not shown) on the distal end 516 of the instruments. The instruments pivot around centers of rotation approximately defined by the incisions in the muscles of the body wall 512.

The tools are selected from among a family of approximately 33 cm long, 5–10 mm diameter surgical instruments. During the operation, the surgeon is frequently working with two toolhandles, while looking away from the patient at a television monitor, which displays the internal worksite image provided by the scope camera.

A representative handle end 518, with a cover piece removed, is shown with reference to FIG. 2, and a representative scissor tool end 516 is shown with reference to FIG. 3. An outer shaft 524 is connected to two jaws 86a and 86b, which are both also hingedly connected to an inner shaft 526, such that when the shafts translate relative to each other, the jaws open, or close, depending upon the direction of relative motion. This type of linkage can be used with grippers, scissors, or other types of jawed tools. There are also other types of linkages. However, in general, all have a relative translation of two shafts that causes opening and closing of gripper or cutting jaws. Typically jawed instruments have two jaws, however, there can be more than two, such as when several jaws are attached to a collar, and are closed by retraction into a narrow sleeve.

In general, the handle 518 incorporates a lever 522, which amplifies the force applied by the human hand by a factor of around four, and transmits this force to the inner shaft 526, which runs the length of the tool to the working end 516. The travel extent of the inner shaft 526 depends on the individual lever design for the brand of tool, typically between 1 and 8 mm. The finger loops 528a and 528b of the handle 518 may be decoupled from the twisting of the outer and inner shafts 524, 526 about their long (parallel to the z) axis. Twisting can be controlled by placing the index finger on a wheel 534 at the top of the shaft. Typically, the inner shaft 526 is coupled to one 528a of the two handles through a ball joint 532 and the outer shaft 524 is held translationally in place by the wheel 534, which has an internal flange that mates with the outer shaft to fix it translationally. The wheel also has a key on its inside that fits into a slot on the outside of the outer shaft, which key/slot pair couple the shaft and wheel rotationally. The wheel fits in an opening in the handle 528b, with respect to which the wheel and outer shaft can rotate about the z axis, as described above. The two handles 528a and 528b are fixed to each other with respect to rotation around the z axis. A cover to the handle (not shown) is essentially congruent with the larger handle piece 528b, trapping the wheel 534, outer and inner shafts 524 and 526, and the smaller handle piece 528a therebetween.

Thus, the wheel essentially permits decoupling rotation of the outer shaft from rotation of the handle. The inner and outer shafts are coupled to each other in a typical tool by the linkages that join each to the jaws, which are connected to each other such that they rotate with each other. There are some tools that do not have a decoupling wheel, and with those tools, rotating the handle around the shaft axis also rotates the outer shaft.

A typical MIS jawed tool has five degrees of freedom, relative to the axes shown in FIG. 1. These are: translation along the z axis, rotation around the z, x and y axes, and motion of the jaws 86a, 86b relative to each other. The insertion force (z axis), pitch and yaw torques (x and y axes), and the jaw force are all significant in surgery and training. Active twisting around the tool (z) axis is not always applied, but is present in many procedures. Translation along the x and y axes does not occur, due to the constraint of the cannula and the patient's body wall 512.

Similar MIS techniques are employed in arthroscopy, retroperitoneoscopy, pelviscopy, nephroscopy, cystoscopy, cisternoscopy, sinoscopy, hysteroscopy and urethroscopy, just to name a few. The common feature of all of these MIS techniques is that they obtain and display a visual image of a worksite within the human body and pass specially designed surgical instruments through natural orifices or small incisions to the worksite to manipulate human tissues and organs, thus avoiding the collateral trauma caused to surrounding tissues, which would result from creating open surgical access. These techniques may be variously referred to herein as minimally invasive surgeries, MIS, generic endoscopies, or key-hole surgeries.

Current MIS technology presents many difficulties. First, the image of the worksite is typically a two-dimensional image displayed on an upright monitor somewhere in the operating room. The surgeon is deprived of three-dimensional depth cues and may have difficulty correlating hand movements with the motions of the tools displayed on the video image. Second, the instruments pivot at the point where they penetrate the body, causing the tip of the instrument to move in the opposite direction to the surgeon's hand. Third, existing MIS instruments deny the surgeon the flexibility of tool placement available in open surgery. Most MIS tools have rigid shafts and are constrained to approach the worksite from the direction of the small opening. Those that include any articulation have only limited maneuverability. Fourth, the length and construction of many MIS instruments reduces the surgeon's ability to feel forces exerted by tissues and organs on the end effector of the tool. Fifth, the MIS tools are not visible on the display near to the entry/exit point, and thus the surgeon's control thereof is blind for a non-negligible distance.

Overcoming these difficulties and achieving expertise in MIS procedures ideally requires extensive training, practice and constant familiarization with conventional and new MIS tools. However, despite surgeons' adaptation to the limitations of MIS, the technique has brought with it an increase in some complications seldom seen in open surgery, such as bowel perforations due to trocar or cautery injuries. Moreover, one of the biggest impediments to the expansion of minimally invasive medical practice remains lack of dexterity of the surgical tools and the difficulty of using the tools, and the attendant difficulties to learn the techniques.

Presently, training is very limited, frequently characterized as a, "see one, do one, teach one," method, which is restricted by the availability of operations that may be used as teaching cases. Such training places a great deal of pressure on a new surgeon (not to mention a new patient). To the extent that "practice makes perfect," the dearth of opportunities for high quality practice impedes the path to perfection. There is also pressure to reduce use of animals in training, if at all possible.

Another difficulty with training is that many actual cases that are available for training are unique, and thus do not offer a general teaching vehicle for typical cases. On the other hand, there are a variety of standard techniques that must be mastered and there are always some that are not required for any particular case. On still another hand, training by only a small number of live operations does not offer the trainee exposure to a wide variety of surgical scenarios, conditions, and pathologies that might be found in a real operating room with a real patient, but which are difficult to recreate with a cadaver, such as the onset of internal bleeding. Further, there is limited opportunity to evaluate surgeons in training in a standardized and objective way. There is also no reliable way to quantify the evaluation of surgeons in training.

Other important information that is difficult to obtain at this time are positions and forces that characterize the surgeons' motions. Such information, including time on task, accuracy, peak force applied, tissue damage, and position error may be potentially used not only to give feedback to the learning surgeons about their performance and progress, but for testing, licensing, and re-validating surgeons. All of the foregoing complications make it difficult to learn and teach MIS techniques.

Thus, there is a great need for a means to teach surgeons these relatively new techniques, without exposing human, or animal patients to undue dangers.

It has been proposed to teach MIS through simulation, of various types. Theoretically, a high fidelity simulation could provide trainees with numerous opportunities for training, performing the same procedure many times. Further, good simulation could simulate many different situations, including the standard, and the non-standard.

Some existing simulation methods use commercially available synthetic (e.g. plastic) torso and organ models for MIS training, as well as cadaver or animal dissection. Synthetic and nonliving tissue can have dramatically different mechanical characteristics than live tissue, and live animal dissections are being phased out for ethical reasons.

The work of doctors at Penn State University College of Medicine revealed that haptic (touch-based) "learning" occurs as surgeons learn MIS. Experienced surgeons are much better at identifying shape and consistency of concealed objects using MIS tools than are medical students (Gorman et al, 1999). (References listed here are set forth in full immediately preceding the claims, below.) Given that haptic information is significant in surgery, it follows that providing accurate haptic sensations to surgeons as they practice is essential.

Thus, another type of simulation is to use a haptic user interface, to display tissue property data taken from live human tissue, through a mechanical simulator. This can offer more realistic reaction forces to the student than working with the synthetic or cadaver simulators.

Any simulation system that simulates both the visual and haptic sensations of surgery would include a basic set of elements. Generally speaking, as shown schematically with reference to FIG. 4, these components include a dual function haptid input and display device 40 and a computer 42, which controls the simulation. Graphics display is provided by a visual monitor 44, and haptic display through an electromechanical force-feedback device 40, usually specialized for the type of surgery being simulated. The user interacts with the simulation through the mechanical interface 46, which measures the instrument position in the simulated workspace, and the user manipulable object 718. The computer interfaces with the mechanical interface through an electronic interface 48. It also runs real-time software, which uses the position (and its derivatives) as the input to tissue models based on simple mass-spring-damper relations, finite element methods, or other techniques, to determine the geometric and dynamic behavior of the simulated tissue. These reactions are fed to software loops, which continuously update the commands to both the haptic 40 and graphical 44 display devices.

Extensive effort has gone into developing each of the basic simulator system elements described above. As the present invention was focused most directly on the haptic display device 40, and the mechanical interface 46, it is helpful to discuss significant work in this field.

Force-feedback devices as a field grew out of efforts initiated in the 1950's and 1960's to develop "master" manipulators for telerobotic applications. A human interacts with the master device to control a second, "slave" device, which performs a task. Telerobotics are generally implemented in environments unfavorable for human manipulation, due to harmful environmental factors or motion constraints, or for tasks that a robot can be specialized to perform. These input devices took on various forms: devices morphologically similar to the slave, joysticks, exoskeletons which encased the hand or more of the body, and more generalized kinematic configurations. See generally, (Madhani., 1998), (Burdea, 1996).

The observation that human performance could be significantly improved by providing force feedback to the system user led to later efforts to develop masters to interact, not with a distant real environment (more, about which, is discussed below, in connection with telesurgery) but with a simulated or "virtual" environment. This led to the introduction of generalized force-feedback manipulators for virtual reality such as the PHANTOM™ haptic interface, which is the basis for a number of the systems described here (Massie, 1993). These generalized force feedback manipulators can be used with a simulated MIS environment, to provide a training simulator.

The trend of using generalized force-feedback manipulators can be seen for the field of medical robotics in particular. Force feedback telemanipulator systems have been introduced to permit motion scaling and filtering for microsurgery and to relieve the kinematic constraints and potential for fatigue on the surgeon in laparoscopy. Examples include an opthalmic telerobotic system developed by Ian Hunter at Massachusetts Institute of Technology ("MIT") (Hunter, 1995) and a laparoscopic system designed by Akhil Madhani, also then at MIT. (Madhani, 1998).

In such systems, forces reflected to the user can be amplified to effectively give the surgeon a "super-human" sense of touch and better control when working with delicate tissues. Some efforts to bring force-feedback into the surgery simulation arena have produced a variety of dedicated haptic devices while others, focusing on achieving sophisticated modeling and graphics, have integrated one or more of generalized devices into their simulations. These configurations are, predominantly, three actuated degree-of-freedom devices (pitch, yaw and insertion), which either actuate around the pivot point or apply forces to the tool tip.

Machines that actuate around the pivot point include the commercially available Immersion Impulse Engine, available from Immersion Corporation of San Jose, Calif., and a device developed by Ecole Polytechnique, the Bleuler Lab (Vollenweider, 1999).

Devices that apply forces to the tool tip include the PHANTOM™ Haptic Interface, available from Sensable Technologies, Inc., of Cambridge, Mass. (Massie, 1993), and described in U.S. Pat. No. 5,587,937, among others, issued on Dec. 24, 1996, in the name of Massie et al, and one disclosed in a recent patent assigned to Immersion Corporation (U.S. Pat. No. 5,828,197) (Martin, 1996). Both the 5,587,937 Massie et al. Pat., and the 5,828,197 Immersion Martin '197 patent are hereby incorporated fully herein by reference.

A modified instance of a PHANTOM™ haptic system, which embodies aspects of the present invention, is shown, in FIG. 5. (Thus, FIG. 5 does not depict prior art. The only aspects of FIG. 5 that are prior art are between the base 51 and the first gimbal link 80.) The PHANTOM™ haptic apparatus is essentially a three DOF manipulator, which is approximately counterbalanced using the weight of two of its own motors 52a and 52b. The standard PHANTOM™ interface uses a passive three DOF gimbal at the end of the actuated three DOF arm 56. Various user manipulable attachments are available, including a stylus and a thimbal. As shown in FIG. 5, the gimbal 54 has only two unactuated DOFs, rather than the standard three. The third DOF is actuated, as used in the present invention, as explained in detail below. A five bar linkage 58 connects the gimbal 54 to the base 60, through the three actuated DOFs.

The Martin '197 Patent also discloses a device for interfacing the motion of a user with a computer system. A modified instance, which embodies aspects of the present invention is shown, in part FIG. 6. (Thus, FIG. 6 does not depict prior art. The only aspects of FIG. 6 that are prior art are between the base 63 and the first link 64 of the gimbal.) It provides three degrees of freedom to the user manipulable object, similar to the PHANTOM™ haptic interface. Three grounded actuators 64 provide forces in the three degrees of freedom. (In contrast, the PHANTOM™ haptic interface, has one grounded actuator 53 and two moving actuators 52a and 52b, which counterbalance the user-held object.) Two of the Martin '197. device degrees of freedom are a planar workspace provided by a closed-loop linkage of members 68. The third degree of freedom is rotation of the planar workspace provided by a rotatable carriage 66. Capstan and cable drive mechanisms transmit forces between the actuators 64 and the user object 62. The drums 70 rotate with the carriage while the pulleys and actuators 64 remain fixed to ground. While this configuration is not balanced like the PHANTOM™ interface, it should decrease the inertia of each of the planar linkage axes. The Martin '197 interface also may include a floating gimbal mechanism coupling the linkage 68 to the user object 62, similar to the PHANTOM interface. One of the user objects shown is a two handled grip 74 that can be used to simulate an MIS handpiece. The Martin '197 Patent. mentions that it might be possible to actuate motion of the handpiece around the tool's long axis (z, as shown in FIGS. 1 and 6), but that this is not recommended, as the need is infrequent in surgery, and the cost would entail heavy actuators. The Martin '197 patent also discloses tracking the relative motion of the two handles, but does not discuss actuating any such motion.

The PHANTOM™ haptic interface and the Immersion Impulse Engine are the two predominant commercially available devices that have been implemented by developers of software simulations to provide force feedback for their systems. Thus, most simulations have feedback to the pitch, yaw, and insertion axes of motion, while the rotation of the tool and the opening and closing of the handles of any gripper/scissors tool, are passive, without actuation or force feedback.

None of the devices described above provide a high fidelity, fully functional simulator for MIS. They do not provide a user interface object that sufficiently replicates the feel and operation of a two (or more) handled gripping/scissoring, tool, such as a gripper, with force feedback upon each of the five DOFs, including the jaw DOF, that are important for such MIS operations.

In addition to the need to train surgeons, there is further the related need to evaluate surgeons as they are learning the MIS techniques, again without endangering patients. Theoretically, a device that simulates MIS could also be used to evaluate trainees, if it could monitor the trainee's motions and applied forces, relative to the surgical environment. However, because there is no device that accurately simulates all of the conditions of MIS, there is also no device that can accurately monitor and quantify them, in particular, the applied forces.

Another opportunity that such a machine, if it were to exist, would fill, is that of surgical planning for even an experienced MIS practitioner. As new or risky MIS tasks are developed, a surgeon may want to try several alternative approaches before the actual surgery. A high fidelity simulator would provide some opportunity to realize this objective.

As has been mentioned, telesurgery systems are being developed to increase a surgeon's dexterity as well as to allow a surgeon to operate on a patient from a remote location. "Telesurgery" is a general term for surgical systems where the surgeon indirectly controls surgical instrument movements rather than directly holding and moving the tools. In a system for telesurgery, the surgeon is provided with an image of the patient's body at the remote location. While viewing the three-dimensional image, the surgeon manipulates a master device, which controls the motion of a servomechanism-actuated slave instrument, which performs the surgical procedures on the patient. The surgeon's hands and the master device are positioned relative to the image of the operation site in the same orientation as the slave instrument is positioned relative to the act. During the operation, the slave instrument provides mechanical actuation and control of a variety of surgical instruments, such as tissue graspers, needle drivers, etc., which each perform various functions for the surgeon, i.e., holding or driving a needle, grasping a blood vessel or dissecting tissue.

The requirements of a user interface to be used in simulation would also meet many of the requirements of a master to be used in telesurgery.

Such telesurgery systems have been proposed for both open and MIS procedures. An overview of the state of the art with respect to telesurgery technology can be found in "Computer Integrated Surgery: Technology and Clinical Applications" (MIT Press, 1996).

Proposed methods of performing telesurgery using telemanipulators also create many challenges. One is presenting position, force, and tactile sensations from the surgical instrument back to the surgeon's hands as he/she operates the telesurgery system, such that the surgeon has the same feeling as if manipulating the surgical instruments directly by hand. For example, when the instrument engages a tissue structure, bone, or organ within the patient, the system should be capable of detecting the reaction force against the instrument and transmitting that force to the surgeon. Providing the master instrument with force reflection helps reduce the likelihood of accidentally damaging tissue in areas surrounding the operation site. Force reflection enables the surgeon to feel resistance to movements of the instrument when the instrument engages tissue.

A system's ability to provide force reflection is limited by factors such as friction within the mechanisms, gravity, the inertia of the surgical instrument and the size of forces exerted on the instrument at the surgical incision. Even when force sensors are used, inertia, friction and compliance between the motors and force sensors decreases the quality of force reflection provided to the surgeon.

Apparati developed by Madhani can be used as slave devices in a telesurgery system. This work is disclosed in several patents and applications, including three patents, all filed on May 16, 1997, as follows: ARTICULATED SURGICAL INSTRUMENT FOR PERFORMING MINIMALLY INVASIVE SURGERY WITH ENHANCED DEXTERITY AND SENSITIVITY, issued Aug. 11, 1998, as U.S. Pat. No. 5,792,135; WRIST MECHANISM FOR SURGICAL INSTRUMENT FOR PERFORMING MINIMALLY INVASIVE SURGERY WITH ENHANCED DEXTERITY AND SENSITIVITY, issued Aug. 25, 1998 as U.S. Pat. No. 5,797,900; and FORCE-REFLECTING SURGICAL INSTRUMENT AND POSITIONING MECHANISM FOR PERFORMING MINIMALLY INVASIVE SURGERY WITH ENHANCED DEXTERITY AND SENSITIVITY, issued on Sep. 15, 1998 as U.S. Pat. No. 5,807,377. Each of these, in turn, claimed priority to Provisional application No. 60/017,981, described in a PCT application, PCT/US98/19508, filed on Sep. 18, 1998, which designated the United States, entitled ROBOTIC APPARATUS, published on Oct. 7, 1999, as WO 09650721A1. All of the above mentioned Madhani patents and applications are incorporated herein by reference.

The Madhani ROBOTIC APPARATUS invention, in general, concerns a robotic apparatus that has seven actuators and a linkage that actuates a two jawed end effector. Three serial macro freedoms have large ranges of motion and inertias, and four serial micro freedoms, nearest to the effector, have small ranges of motion and inertias. The macro and micro freedoms are redundant. Translation of the end effector in any direction is actuated by at least one micro joint and at least one macro joint. This arrangement facilitates fine control of the force that the end effector applies to its environment. The apparatus can be part of a master and slave combination, providing force feedback without any explicit force sensors. The slave is controlled such that a slave having more DOFs than the master can be controlled. A removable effector unit actuates its DOFs with cables. The Madhani documents describe a master that is based on the PHANTOM™ haptic interface identified above. The Madhani slave can include a pair of endoscopic jaws or blades, such as a gripper or scissors. It also discloses a simple type of two element user interface that is used with a PHANTOM™ haptic interface, shown in FIG. 20 of the ROBOTIC APPARATUS application, which comprises a pair of tweezer-like members that are hinged to each other and coupled to a spring that causes their return to a rest open position. The document mentions generally that they may be actuated by an actuator located at their joint.

What is needed, therefore, for telesurgery is a servomechanical surgical master apparatus that can provide the surgeon with sensitive feedback of forces exerted on the surgical instrument. What is needed for training is a surgical simulator that realistically simulates the conditions of a minimally invasive surgery. Both such systems require a user interface that replicates the tools that the surgeon would use, including a jawed tool, such as a gripper or scissors and that presents to the user the forces that would arise during an actual surgery, including both tool handle open/close forces (e.g., gripper, scissors) and forces that arise upon rotating the tool handle around its long (2) axis. Such a device should feel to the user as real as possible, with as little added friction and inertia as possible, thereby enabling tissue diagnosis and manipulation, both simulated, and telerobotic. It should be possible to incorporate such a device into a simulated model that closely approximates a human body. The device must be robust and must have a range of motion and force possibilities that coincide with those experienced in actual MIS.

SUMMARY

In general, a preferred embodiment of the invention is a robotic handle module that actuates handles of a user interface for various types of robotic applications, including MIS. A modified, standard MIS tool handle has a pair of parallel shafts that translate relative to each other upon relative motion of the handles. They are free to rotate relative to each other. A housing engages the two shafts of the tool handle. The first shaft is translationally fixed and rotatably free relative to the housing. The first shaft is coupled to an actuator that actuates rotation of the first shaft relative to the housing. An encoder associated with the actuator measures (indirectly) the rotation of the shaft. The second shaft is coupled to the housing such that it is rotationally fixed about and translatable along the axis of its elongation. The second shaft is fixed to a cartridge that is slidably coupled to the housing. The cartridge constitutes a linear capstan and translates relative to the housing, in response to relative translation of the two shafts. A jaw action actuator is coupled to the cartridge through a cable drive, and can actuate the relative translation of the two shafts, and thus, the two handles. An encoder associated with the jaw action actuator measures (indirectly) the relative translation between the two shafts. Thus, under proper control, the jaw action actuator can actuate jaw action of a tool in a tool environment, either virtual, or actual, as in a slave environment. Thus, the handle module can actuate both the jaw action of a jawed tool, as well as rotation around the long axis of the shafts. The actuation thus may also provide force feedback to the user, for use as a simulator, or telerobotic master.

A preferred embodiment of the invention is a haptic apparatus to interface a human user with a tool environment through the interchange of force. The apparatus comprises a user contact element for physically contacting a body member of the user, the contact element comprising a pair of first and second contact members that are movable relative to each other. The apparatus further comprises a first elongated member that is translationally fixed to the first contact member, and a second elongated member that is parallel with the first elongated member, and that is coupled to the second contact member, such that the second elongated member is translatable relative to the first elongated member upon relative motion of the first and second contact members. The second elongated member is also rotatable relative to the first elongated member upon rotation of the first contact member relative to the second elongated member. The apparatus also includes a first actuator, which is coupled to both of the first and second elongated members, such that upon actuation the first actuator actuates relative translation of the first and second elongated members. The apparatus also includes a second actuator, which is coupled to both of the elongated members, such that upon actuation, the second actuator actuates relative rotation of the first and second elongated members about an axis parallel to their axes of elongation.

In a typical embodiment, the first and second elongated members are substantially concentric shafts, the first being a hollow outer shaft that surrounds the second, which is thus an inner shaft.

The contact element may be a two handled element, with the first and second contact members constituting the handles, being rotatable relative to each other about an axis that is perpendicular to the axis of elongation of the first and second shafts. The handles may be rotatable, like scissors handles, or translatable (as are scissors handles, or, more definitely, as are the two components of a syringe).

In yet another preferred embodiment of the invention, the handle element is a two-handled minimally invasive surgery, handpiece such as is used for endoscopy or laparoscopy, including graspers, scissors and grippers.

The apparatus may include displacement sensor arranged upon activation to generate a signal that corresponds to the relative translational and/or rotational displacement between the first and second elongated members.

According to another preferred embodiment, each actuator has a nominally stationary part and a nominally movable part. The apparatus further comprises a housing, to which the stationary part of both actuators are attached, the outer (first) elongated member being rotatably coupled and translatably fixed to the housing and the inner (second) elongated member being rotatably fixed and translatably coupled to the housing.

The rotor of the first actuator may be coupled to the inner elongated member such that actuation of the first actuator actuates relative translation between the inner elongated member and the housing, and thus, between the inner and the outer elongated members. The coupling between the first actuator and the inner elongated member may be a cable transmission that includes a cartridge that is fixed to the inner elongated member, and that is translatably coupled to slide along an axis, relative to the housing, the translation of the cartridge being actuated by the first actuator.

According to still another embodiment, the second actuator is a rotary motor, and is coupled to the outer elongated member, such that the second actuator actuates relative rotation between the outer elongated member and the housing, and thus between the outer elongated member and the inner elongated member.

Yet another preferred embodiment includes first and second displacement sensors arranged upon activation to sense the relative translational and rotational displacement, respectively, between the first and second elongated members, and to generate signals that correspond thereto. The sensors are coupled to a controller that is coupled to the first and second actuators, and that is further arranged, upon activation, to control the first and second actuators based, in part, upon the signals from the displacement sensors.

Typically, the first actuator is arranged with its axis substantially perpendicular to the first elongated member, and the second actuator is arranged with its axis substantially perpendicular to that of the first actuator.

In another preferred embodiment, the controller is configured to actuate the first actuator to present forces to a user engaging the contact members that simulate minimally invasive surgery tool jaws urged against a resisting force, such as a gripper gripping tissue, or spreading apart tissue, or as scissors cutting through tissue. The controller may also be configured to actuate the first actuator to present forces to a user engaging the contact members that are proportional to their relative velocity, thereby simulating a damping factor relative to their motion, or their relative displacement, thereby simulating an elastic spring factor.

According to still an additional preferred embodiment, the invention includes a base mechanical interface unit that comprises an interunit link that is fixed to the housing and a powered base linkage that couples the interunit link to a base foundation. The interunit link is movable through at least five degrees of freedom relative to the base, whereby the powered base linkage is arranged, upon activation, to actuate the interunit link and thus the housing, with respect to at least three degrees of freedom of motion relative to the base foundation. The powered base linkage may be either a tip actuated linkage or a pivot actuated linkage. Examples of tip actuated linkages include a PHANTOM haptic interface, as shown in FIG. 5 herein, or a Martin '197 haptic interface, as shown in FIG. 6 herein.

In accord with still another preferred embodiment of the invention, the tool environment may be a slave robot that is configured to be operated by the haptic interface apparatus as a master device. The apparatus further comprises a controller coupled to the slave apparatus, configured upon activation to control its motions and a communications channel, coupling the controller for the master apparatus to the controller for the slave apparatus. The slave robot may be a minimally invasive surgery apparatus for use upon a subject, having an end effector with two actuate d members that are movable relative to each other under actuated control, such as grippers or scissor jaws, and which contact the subject in use. The actuated end effector members may further be rotatable together around an axis under actuated control In line with this embodiment, the haptic interface controller may be further configured to: receive signals through the communications channel from the slave robot that correspond to any force that the actuated end effector members experience if contacting the subject while actuated to move relative to each other; and to actuate the first actuator to actuate relative rotation of the user contact members to present a force to a user in contact with the user contact members that corresponds to any such force that the end effector members experience upon moving relative to each other. Similarly, the controller and components may be further configured to present a force to a user in contact with the user contact element, which corresponds to any force that the end effector members experience upon rotating together.

According to yet another preferred embodiment, the invention is a haptic apparatus to interface a human user with a tool environment through the interchange of force. The apparatus comprises a user contact element for physically contacting a body member of the user. The contact element comprises a two-handled minimally invasive surgery handpiece with a pair of first and second loop handles that are movable relative to each other. The apparatus further comprises a first, outer elongated member that is translationally fixed to the first loop handle and a second, inner elongated member that is concentric with and inside the first elongated member, and that is coupled to the second loop handle, such that the inner elongated member is translatable relative to the outer elongated member upon relative motion of the two loop handles. The outer elongated member is also rotatable relative to the inner elongated member upon rotation of the first loop handle relative to the inner elongated member. The apparatus also comprises an actuator, having a stator and a rotor, which actuator is coupled to both of the outer and inner elongated members, such that upon actuation the actuator actuates relative translation of the inner and outer elongated members. Also part of the apparatus is a housing, to which the stator is attached. The outer elongated member is rotatably coupled and translatably fixed to the housing and the inner elongated member is rotatably fixed and translatably coupled to the housing. The rotor is coupled to the inner elongated member such that actuation of the actuator actuates relative translation between the inner elongated member and the housing, and thus, between the inner and the outer elongated members.

Yet another preferred embodiment of the invention is a minimally invasive surgery simulator apparatus comprising a handle unit, a handle actuation module and a base mechanical interface. The handle unit includes a pair of handles that correspond to handles of a minimally invasive tool and a pair of parallel elongated members that translate relative to each other along their axis of elongation and that rotate relative to each other around the axis of elongation, each being coupled to a respective one of the handles. The handle actuation module comprises a housing. The first elongated member is rotatably coupled and translatably fixed to the housing and the second elongated member is rotatably fixed and translatably coupled to the housing. The handle actuation module also includes a backdrivable first actuator, the stator of which is coupled to the housing, and the moving part of which is coupled to the second elongated member, such that the first actuator actuates relative translation between the pair of elongated members. A sensor generates a signal that corresponds to translation displacement between the two elongated members. The base mechanical interface unit comprises a handle actuation module support, to which the housing is fixed, and a base foundation, coupled to the handle actuation module support, such that the handle actuation module is movable through at least three additional DOFs relative to the base foundation. The base mechanical interface unit also includes a plurality of backdrivable actuators, coupled between the base foundation and the handle actuation module support, such that upon activation, the plurality of actuators actuates motion of the handle actuation module support relative to the base. The base unit also includes a sensor assembly that generates a signal that corresponds to displacement between the handle actuation module support and the base foundation, relative to the at least three additional DOFs The handle actuation module may further comprise a backdrivable second actuator, the stator of which is coupled to the housing, and the moving part of which is coupled to the first elongated member, such that the second actuator actuates relative rotation between the pair of elongated members. A sensor generates a signal that corresponds to rotational displacement between the two elongated members. A linear capstan may couple the first actuator to the second elongated member and a cable drive and rotary bearing may couple the second actuator to the first elongated member

BRIEF DESCRIPTION OF THE DRAWINGS

These and other features, aspects, and advantages of the present invention will become better understood with regard to the following description, appended claims and accompanying drawings, where:

FIG. 15 shows schematically a plan view of a rotary action drum of a linear capstan embodiment of the present invention;

FIG. 16 shows schematically an arc-section embodiment of the present invention;

FIG. 17 shows schematically, in partial cross-section, a ballscrew embodiment of the present invention.

DETAILED DESCRIPTION

Figure 1:
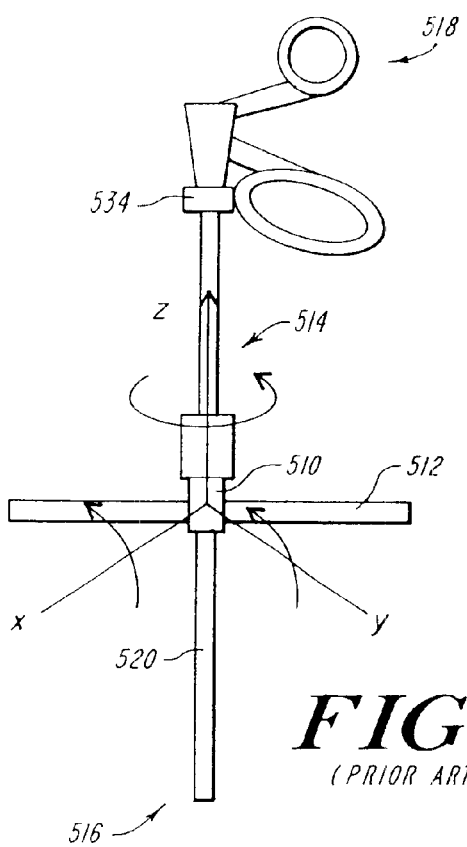
FIG. 1 shows schematically a typical MIS set up of the prior art, showing a body wall, cannula, tool extension tube, and handles.

One embodiment of the invention is a robotic master, that can interface with either a virtual environment, or a slave apparatus in a physical environment. The apparatus has a unique user input module and a base mechanical interface, such as a modified PHANTOM™ haptic interface, or a Martin '197 interface. The user input module, in a representative embodiment, is shown with reference to FIG. 5. A preferred general embodiment of the invention is shown schematically with reference to FIGS. 5 and 7. A base mechanical interface 50 provides three actuated degrees of freedom to an end of a shaft 56, to which a gimbal 54 is attached. The gimbal has a link 80 that rotates around axis $G_1$ relative to the shaft 56 and another link 82 that rotates around the axis $G_2$ relative to the link 80. This second gimbal link 82 constitutes an interunit link between the jaw module and the base mechanical interface. The mechanical base interface actuates the gimbal with respect to three degrees of freedom relative to the base foundation 51.

A handle actuation module 84 is fixed with respect to rotation and translation relative to the second gimbal link 82, such that they move together. The handle actuation module couples the base mechanical interface 50 to a handle unit 18, which is essentially identical to a standard gripper or scissors handle unit, as described above. The handle unit has a user contact element, that is typically made up of two user contact members. It has a pair of handles 28a and 28b, one of which 28b is coupled to an outer shaft 24, through a wheel, and one of which 28a is coupled to an inner shaft 26 through a ball joint, concentric with the outer shaft , so that both shafts can rotate relative to the handles. The handles constitute members that the user contacts and manipulates to use the interface tool.

Figure 3:
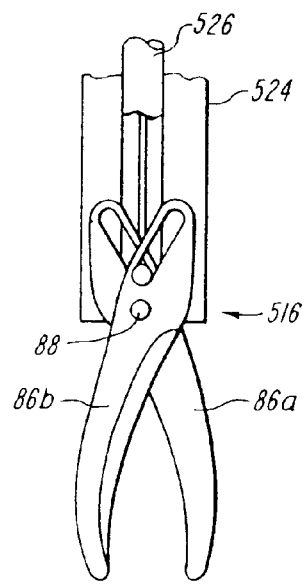
FIG. 3 shows schematically an end effector portion of a typical jawed scissors MIS tool of the prior art.

As explained below, the handle actuation module 84, in conjunction with the base mechanical interface 50, presents forces to the user that simulate moving and operating the jaws of an actual jawed tool. In the present invention, relative motion of the handles 28a and 28b causes relative translation of the inner and outer shafts 26 and 24. However, there is no end effector at the other end of the shafts, such as a gripper as shown in FIG. 3. Instead, each shaft is coupled to the handle actuation module 84, as explained below, which is shown in more detail with reference to FIG. 7.

The handle actuation module 84 has a housing 88. The housing 88 is rigidly coupled to the second gimbal link 82. Within the housing 88, a cartridge 90 is slidably carried. The inner shaft is translatably coupled and rotatably fixed relative to the housing. The outer shaft is translatably fixed and rotatably coupled to the housing, as explained below.

A first actuator 92, as shown, a rotary motor, is fixed to the housing such that its stator is stationary relative to the housing, and its rotor rotates relative thereto. The first actuator rotor is coupled to the cartridge 90 through a cable 94, which is wrapped around the capstan 114 of the rotor, and is coupled to the cartridge 90, for instance with a cable terminator in a mating hole, described in more detail below. The cartridge 90 is slidably coupled to the housing, so that the cartridge can slide along the z axis (parallel to the long axis of the inner and outer shafts 26 and 24), but so that the cartridge is fixed relative to the housing 88 for any other motions. This is discussed in more detail below, in connection with FIGS. 10 and 11. This first actuator 92, and the components associated with it may be referred to below as the jaw action actuator, or components.

The cartridge 90 is also fixedly coupled to the inner shaft 26 so that translation of the inner shaft along the z axis causes translation of the cartridge, and back drives the actuator. Actuation of the actuator causes relative translation of the inner and outer shafts. The inner shaft may be clamped to the cartridge 90 with a set screw 130 and a flexure or clamping bar 128.

It shall be understood that, as used herein, an actuator that actuates a type of relative motion between two members is also backdriven by corresponding relative motion between the same two members. Thus, the jaw action actuator actuates relative translation between the inner and outer shafts, and is also backdriven by relative translation of the inner and outer shafts, typically by the user's motion of the handles. Thus, the user may receive force, or haptic feedback from the handles, and may also control the motion of the handles.

A second actuator 96 is also coupled to the housing 88 through a bracket 98, such that its stator is fixed relative to the housing. The second actuator's rotor capstan 100 is coupled to the outer shaft 24, for instance through a cable 102 and drum 104, connected to a first race of a bearing (not shown in FIG. 7), the second race of which is also connected to the housing 88. Thus, rotation of the outer shaft 24, which arises if the user rotates the handles together around the z axis, causes rotation of the capstan 100 of the second motor 96, and back drives the second actuator 96. Conversely, actuation of the capstan 100 can present a torque around the z axis to the outer shaft, which torque attempts to rotate the handles, and is thus felt by a user who grasps the handles. The second actuator 96 and the components associated with it may be referred to below as the rotary action actuator and components.

Figure 2:
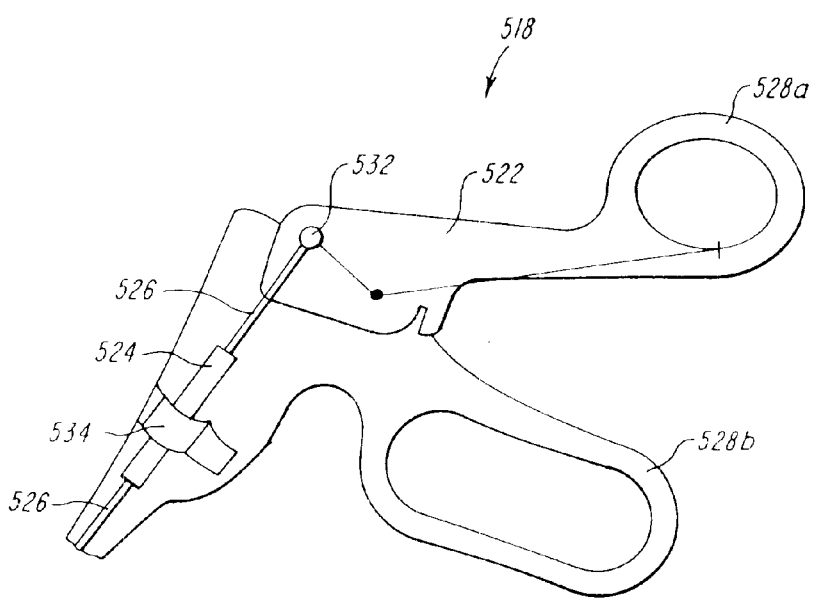
FIG. 2 shows schematically a handle portion of a typical jawed MIS tool of the prior art, such as grippers or scissors.
Figure 4:
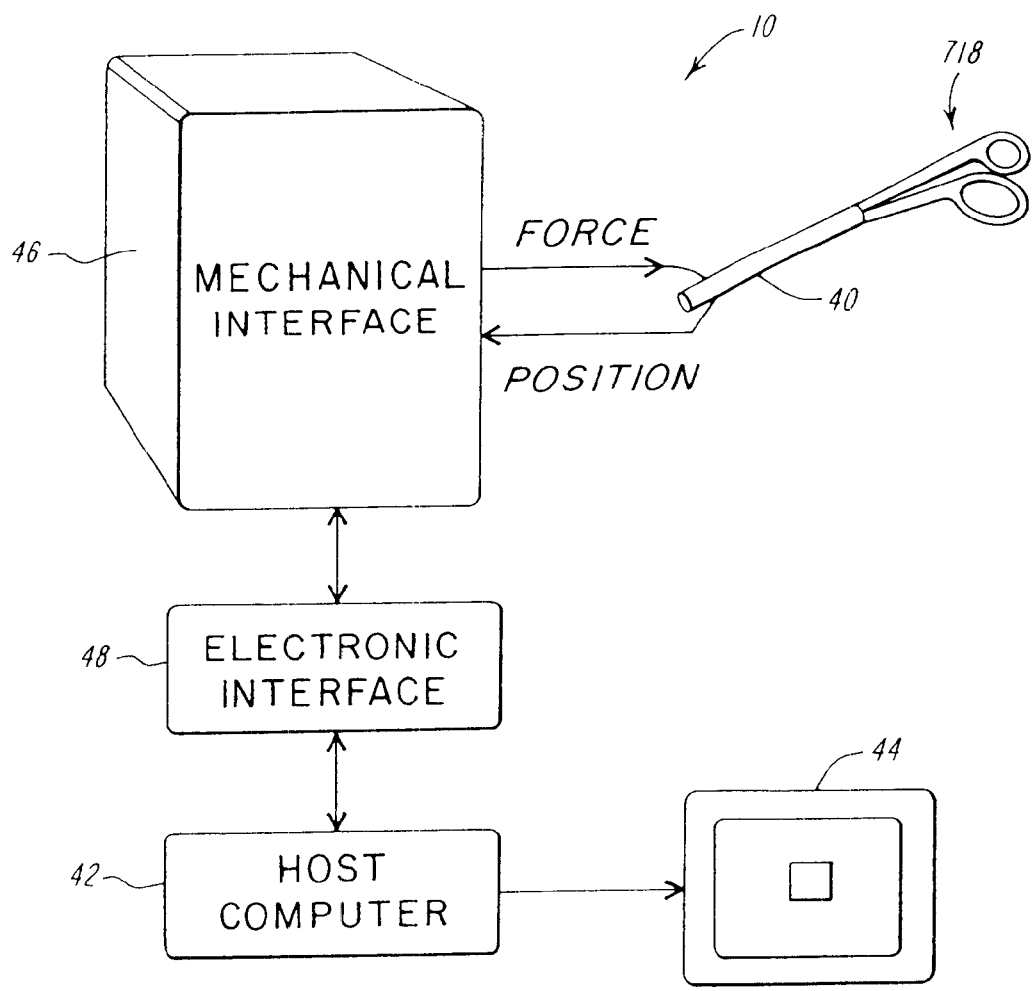
FIG. 4 shows schematically an MIS system of the invention, having a user interface for a two handled MIS tool, a mechanical interface, an electronic interface, a host computer and a visual display.

The inner and outer shafts are free to rotate relative to each other, due to a ball joint connection between the inner shaft and the handle 28a (as shown in FIG. 2 for a standard handle of this type). This is a standard arrangement for typical MIS tools.

The first and second actuators also may include encoders, such that their rotary locations are always known, or are calculable by the controlling computer 42. Alternatively, the encoders may be separate and located elsewhere. In any case, some means must be provided to measure the motion of the shafts, both translationally and rotationally as is conventional in the art.

Thus, a typical operation, if used as a simulator, would be that the user grasps the handles 28a, 28b, and uses them as if they were part of an actual MIS instrument. A computer displays on a monitor a simulation of what would be seen by an MIS camera, based on a model of an operation environment, e.g., a patient's internal body environment; organs, volumes, spaces, tissues, tool end effectors etc. This environment is modeled as to the locations and physical properties of the patient's body. As the user moves the handles, in and out along the z axis, around the z axis, tipping around the x and y axes, as shown in FIG. 1, the computer determines what sort of force/torque would be felt in a physical operation, and controls the three base actuators 52a, 52b and 53, to actuate forces that arise due to the x axis translations and y and z axis rotations. It also controls the two handle module actuators 92 and 96 to actuate forces that arise due to the handles opening and closing and rotation around the z axis, respectively. Thus, the user is presented with all of the types of forces that are present in a physical operation.

Figure 8:
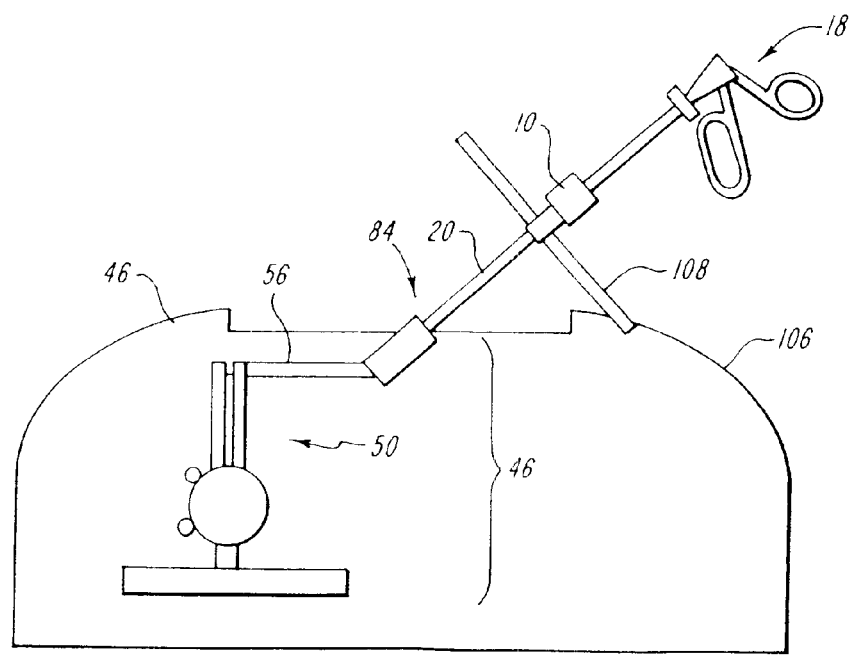
FIG. 8 shows schematically an embodiment of the present invention configured as part of a simulator in a synthetic body portion.

FIG. 8 shows how a simulator of the invention may be arranged. The mechanical interface 46 is hidden within a synthetic body portion 106. The body may have a removable panel 108, which is shown removed. A cannula 10 is placed through this removable panel. The tube 20, which comprises the outer shaft 24 and the inner shaft 26, passes through the cannula, and is coupled to the handle module 84, as described above. With the removable panel in place, and with the simulated body 106 draped as in an operation, the environment faithfully reproduces that which would be encountered in an operating theater. The surgeon manipulates the tool handles, as described above, and the computer and actuators respond to present forces and torques to the user that would be expected to be encountered in an actual operation.

Representative Configurations

The ranges of motion of each of the degrees of freedom, vary with the procedure performed. Pitch and yaw motions around the x and y axes may reach a maximum of 60° from vertical during cholecystectomy and as much as 80° or more during the exploratory phases of a hernia repair. The tool insertion setpoint (an average "home" position, about which the tool moves in both directions) for a surgery varies from near the surface (the tool frequently retracted into the trocar) for hernia repair, to as deep as six inches (15.24 cm) during a cholecystectomy. Departure from this point is typically around three inches (7.6 cm). Finally, the maximum displacement for the roll about the tool z axis, that is the extent to which the surgeon twists the tool, is less than 90° to either side of the rest position, for a total of 180° of motion. There is rarely cause to rotate the tool more than this, and it is never rotated greater than 360°. The proximity with which two tools may approach, or appear to approach, one another places much more stringent constraints on the volume of the device. There is frequently a need to use two tools "like chopsticks and spread" tissue during exploration, for instance, in a hernia repair operation. In this process, the tools are crossed and come within one or two centimeters of one another. However, tool proximity is not as marked in the cholecystectomy. The foregoing parameters will vary for a particular procedure.

Figure 5:
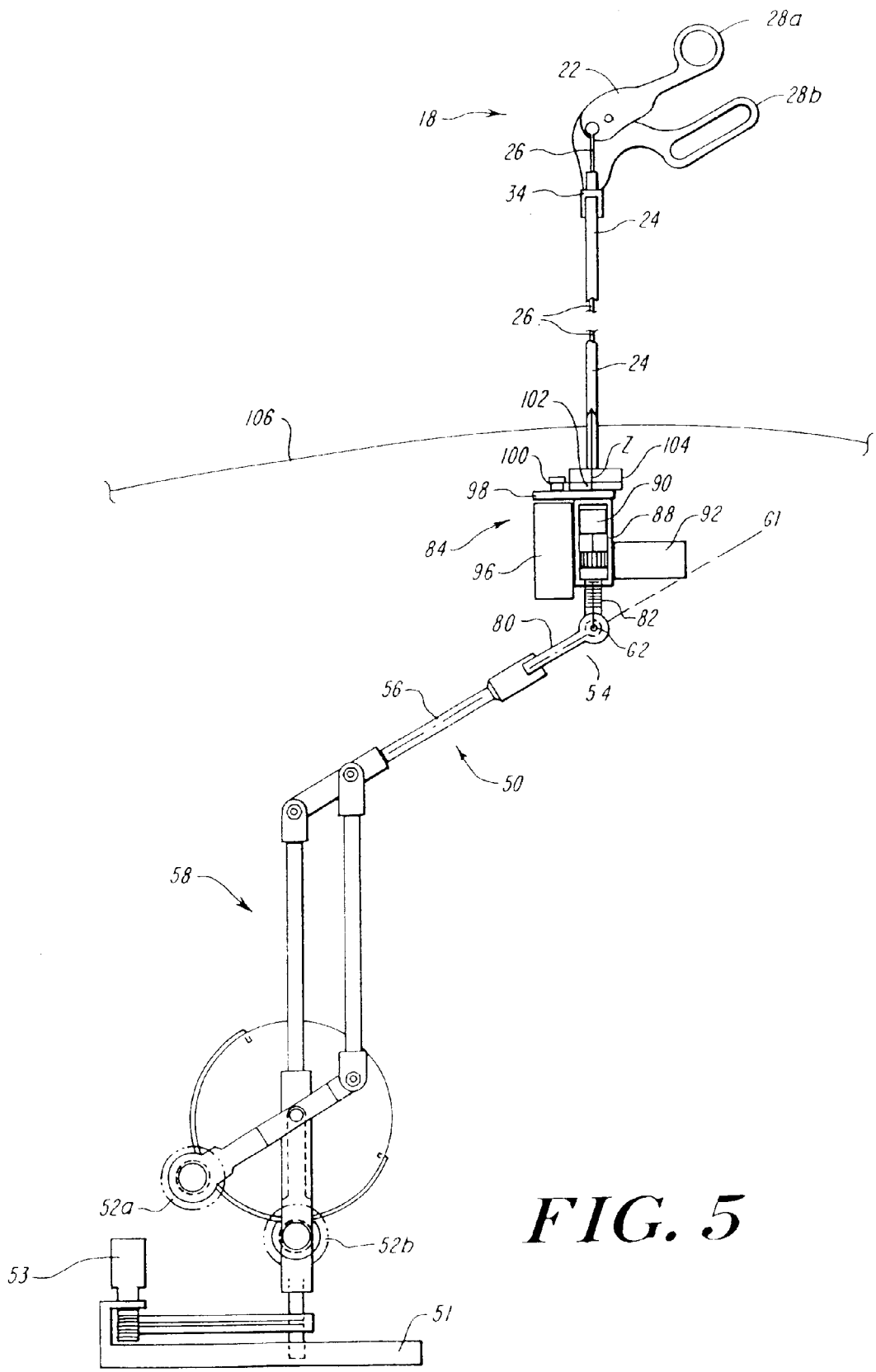
FIG. 5 shows schematically an embodiment of the present invention using a PHANTOM™ type base mechanical interface and a linear capstan handle module.

In a representative embodiment of the handle module, specific device parameters were chosen, as explained below. In the sections following, considerations for generalization of these parameters are discussed. A PHANTOM™ haptic interface, model 1.0 SW (Standard Workplace), available from Sensable Technologies, Inc., of Cambridge, Mass., was used as the basis for the base mechanical interface 50 of a preferred embodiment, as shown in FIG. 5. It was modified by removing its three DOF passive gimbal and replacing it with a two degree of freedom gimbal, identical in functionality to the PHANTOM™ gimbal, but with position encoders at the respective joints. An encoded gimbal is also available from Sensable Technologies Inc. Alternatively, rather than using encoders, the position of the tool tip can be deduced from the position of the gimbal, which is tracked by the base mechanical interface 50, and the position and orientation of the trocar. The modified second gimbal link 82 was constructed to engage the housing 88.

The rotary axis ideally requires a minimum travel of 180° and a torque of 0.08 Nm, and the linear jaw (z) axis required a travel of up to 6 mm and a force of 17 N. For design purposes it was assumed that the actuators and transmissions should provide at least twice the force or torque specified. The first and second actuators 92 and 96 are 16 mm diameter, 4.5 W, 5.44 mNm maximum continuous output brushless rare earth (RE) motors weighing 40 g, having a short term recurring overload capability of up to 25 mNm, available from Maxon Motor A.G., of Sachseln, Switzerland. For the jaw actuator, an integral 19:1 planetary gearbox version of the motor is suitable. For the rotary axis actuator, a 4.4:1 planetary gearbox motor may be used with a cable transmission of 3.3:1 or greater. The jaw actuator has an integrated 13 mm diameter digital magnetic encoder, with quadrature output. At four counts per cycle and sixteen cycles per revolution, this gave a resolution of 0.016 mm per count. This en coder implementation avoids count skipping, which may arise if the encoder resolution is too fine. The same actuator/encoder can also be used for the rotational axis motor 96, yielding a final resolution of 0.36 degrees per count.

Gripper Actuation

Cabling

Figure 9A:
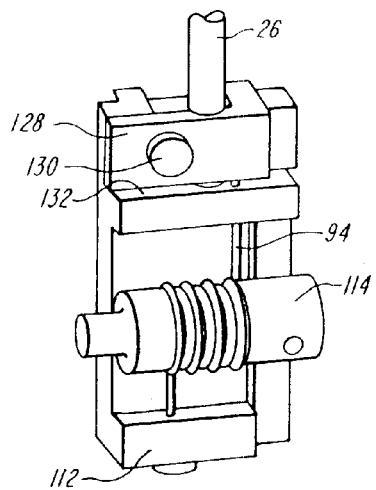
FIG. 9A shows schematically a perspective front view of a cartridge of a linear capstan embodiment of the present invention.
Figure 9B:
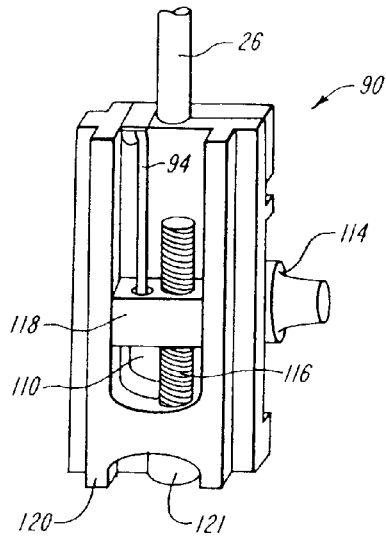
FIG. 9B shows schematically a perspective rear view of the cartridge shown in FIG. 9A

The cabling layouts efficiently use existing space and avoid fatiguing the cables by keeping radii over which they travel as large as possible. The cabling for the jaw axis is shown in FIGS. 9A and 9B. The stationary end 110 of the cable 94 is terminated directly in the base 112 of the cartridge 90 so that the first length of cable would not be required to turn any corners. A 0.25" (0.635 cm) diameter capstan 114 was used with a 0.024" (0.61 mm) steel 7×19 cable 94 available from Sava Industries, of Riverdale, N.J. This cable can carry a 17 N load with a safety factor of 8.8. The capstan has a thread size of ¼20 (31.7 per cm), which provides ample space to securely seat and orient the cable. Four wraps of cable 94 around the capstan 114, when fully tensioned, securely fixed the cable and prevented any slipping. Since total displacement was less than one revolution for the capstan, space for only one thread diameter of cable travel was required.

The back of the cartridge 90 (shown in FIG. 9B) provides space for, and accessibility to, the cable tensioning mechanism 116. The cable was terminated in a block 118, which was free to slide in a long groove in the back of the cartridge. A threaded hole in the block allowed it to be cinched in by a screw 121, anchored in the "fin" structure 120 of the cartridge 90, discussed below. The accessibility is of particular importance because the cartridge and capstan may need to be placed inside the main housing 88 before the cable 94 can be fully tensioned. As such, the cable was brought straight up from the capstan 114 to and over the top of the cartridge and down to the block 118, near the bottom of other side, opposite the capstan.

Cartridge

Figure 10:
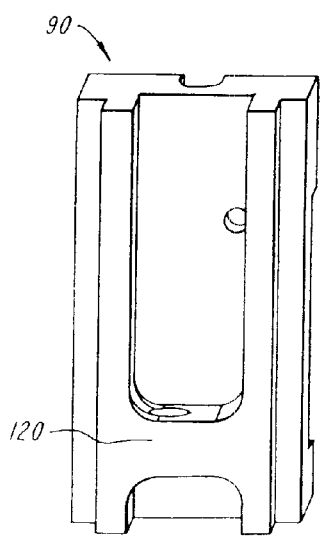
FIG. 10 shows schematically a perspective back view of a cartridge of a linear capstan embodiment of the present invention.
Figure 11:
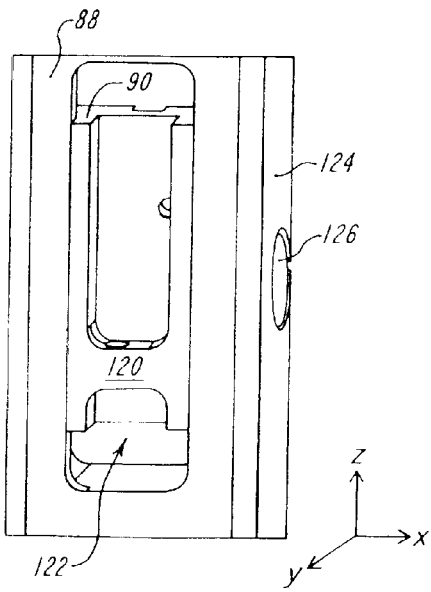
FIG. 11 shows schematically a perspective back view of the cartridge shown in FIG. 10 engaging a housing.
Figure 12:
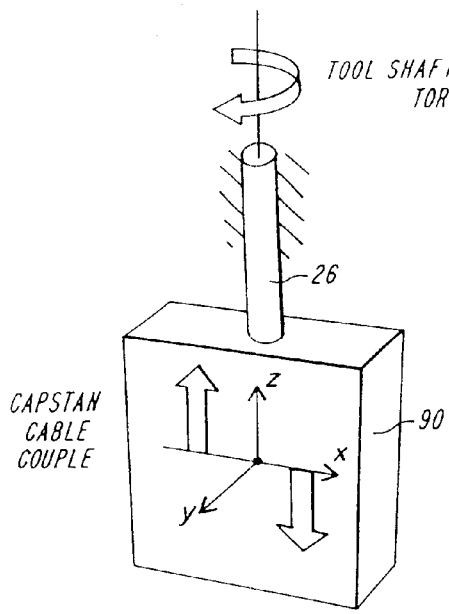
FIG. 12 shows schematically forces and torques that are applied to a cartridge of a linear capstan embodiment of the present invention.

A suitable design for the cartridge and housing assembly is shown with reference FIG. 10, showing the cartridge 90, alone and FIG. 11, showing the cartridge 90 and the housing 88 together. Before examining these structures in detail, it is helpful to understand the torques and forces that are applied to the cartridge, shown schematically with reference to FIG. 12.

A predominant moment is imposed on the cartridge 90 about the y axis by the force couple resulting from the tension in the cable 94 wrapped around the capstan 114. A secondary moment that may be present results from any friction between the inner 26 and outer 24 shafts of the MIS tool, that might arise due to their relative rotation. The friction would induce a twisting moment about the z, or tool shaft, axis. In the ideal case, the cartridge is fully constrained to resist moments about the x and y axes, since the inner tool shaft 26, whose end is fixed in the cartridge 90, is guided by the outer shaft 24, which is in turn fixed in the main housing 88. However, imposing the cable-induced moment in the real world causes the inside shaft 26 to bind within the outer shaft 24 and to possibly cause the inside shaft 26 to deflect. Furthermore, this constraint would not resist the twisting moment about the z, or tool shaft, axis. It is desired to constrain these three rotations, without placing any further geometric constraints on the assembly, so that the insertion of the shaft would fully locate the gripper cartridge without overconstraining it.

One means of accomplishing the foregoing is to provide the cartridge with a "fin" 120, and the housing with a mating slot 122, in which the fin slides. The slot and fin are sized to prevent rotation around the y and x axes. As shown with reference to FIGS. 10 and 11, the fin structure 120, and slot 122 are both generally rectangular, with flat, parallel sides of the fin mating with flat, parallel sides of the slot. The range of motion along the z axis for the cartridge 90 is larger than the possible travel of the actual tool shafts, dictated by the range of rotation motion of the handles 28a and 28b. Thus, the physical end-of-travel stops for the jaw axis can be those on the particular tool handle being used, and the handle module would not need to bear such bottoming out loads. Further, this simulates reality.

Clearance is established between the outer sides of the cartridge and the housing so that there is not redundant constraint on motion along the x axis. Only the fins make contact, not the side walls of the cartridge. Furthermore, since two orthogonal surfaces of the gripper cartridge 90 slide on the back of the housing 88 (the back of the cartridge and the sides of the fins), the material of the back of the housing in which the slot resides, should be friction-reducing. Thus, the entire housing may be ABS (acrylonitrile-butadiene-styrene) or polyacetal, such as sold under the tradename Delrin® by DuPont, DeNemours and Co. The cartridge may be made of steel. Alternatively, the cartridge can be low-friction material and the housing can be metal, or low-friction plates can be located therebetween.

The fin 120 extends along the full length of the cartridge 90, and lies flush with the back of the housing 88. This design has very low friction between the cartridge and housing. The force couple from the tensioned cable also applies a significant moment to the capstan 114, and thus the shaft of the motor. It is possible to use two cables to make the load symmetrical. However, this would require added space and increased complexity. A simpler alternative is to place a bearing in the side wall 124 of the housing 88 opposite the motor, so that the motor shaft is supported on both ends. A hole 126 in which the bearing resides is shown in FIG. 11. This essentially overconstrains the capstan shaft 114, since it attempts to align a third bearing with the pair of bearings inside the first motor 92. Care should be taken in machining all associated dimensions in order to prevent this from becoming a problem.

The design has the outer shaft 24 coupled to the housing 88, through a rotary bearing and the inner shaft 26 fixed in the gripper cartridge 90. The mechanisms for securing these shafts serve not only mechanical considerations but also human use ones. Mechanical concerns include resisting axial forces without backlash or compliance, and providing a long enough contact surface along the z axis to resist moments. Human use concerns are that each of these connections needs to be released and then re-engaged with each change of trocar position in the simulated body. Thus, a number of parameters associated with connecting/disconnecting the mechanism are important: the number of steps involved, number and kind of tools required, number and size of loose parts, and ease of access to the required parts.

The inner shaft 26 is secured to the cartridge 90 by any suitable means. One suitable means is shown in FIG. 9A. A flexure clamp 128 has a screw 130 that faces out of the main housing cavity. A stop surface 132 serves as a hard stop for insertion of the inner shaft 26. The screw 130 is to be adjusted by the user in setting up different trocar positions. Thus, it, and all other such user-adjustable bolts, may have the same interface, such as phillips, flat, etc., to signal its function. In distinction, the other bolts may be cap screws, or allen head. This demarcation may minimize accidental unintentional loosening of screws that should not be loosened, such as those which tension the cables.

It may be found that under some circumstances, the flexure 128 deforms plastically after several cycles, making it difficult to reinsert the tool shaft. To minimize this risk, this piece can be fabricated out of a more elastic material, such as ABS or Delrin® (to save weight) or steel. Alternatively a two-piece clamp similar to that designed for the rotary coupling discussed below, can be used.

Rotary Axis Actuation

Figure 13:
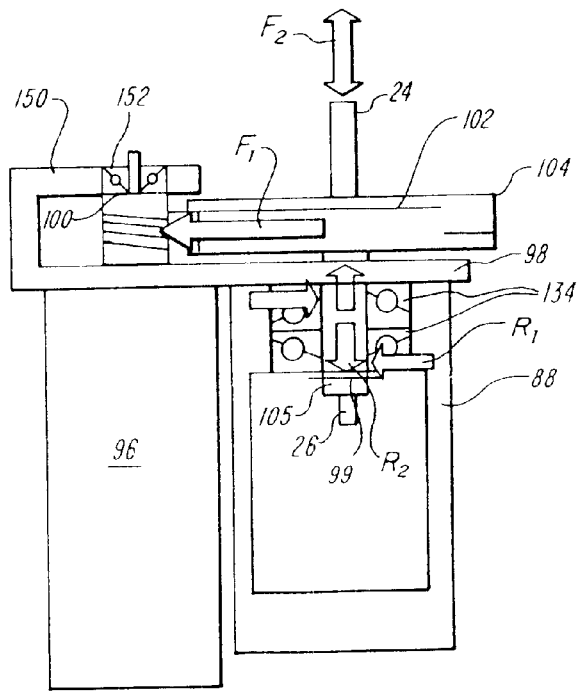
FIG. 13 shows schematically forces and torques that are applied to a housing and drum of a linear capstan embodiment of the present invention.

The rotary actuation is achieved by the second actuator 96, and the cable transmission connected to the outer shaft 24. Proper constraint of the axis of motion is an important concern. The axis design and a schematic depicting applied forces and their reactions are shown in FIG. 13. (In FIG. 13, the cartridge 90 is no t shown, for simplicity.) In this case, the first relevant force $F_1$ is that of the cable 102 pulling the drum 104 and rotor capstan 100 towards one another when the cable 102 is to be tightened. Secondly, forces $F_2$ in both z axis directions along the tool shaft are induced when the simulator resists insertion and withdrawal motions by the user, and in reaction to the handle actuator forces.

Forces exerted on the shaft by cable tension and handle forces are indicated as $F_1$ and $F_2$ and reaction forces are indicated as $R_1$ and $R_2$ respectively. The cable forces tend to tip the cantilevered shaft 24 axis toward the capstan 100, inducing a force couple at the end of the shaft 24, rotationally fixed in the housing 88. Thus, it is preferable to support the shaft 24 with a pair of bearings 134, thus offering a better support spread for resisting this moment. It is also a possibility to support either or both of the shaft 24 and the motor 96 capstan 100 by a non-cantilevered fashion, as discussed below.

The outer tool shaft is secured to the drum 104, as discussed below. The drum 104 is secure d to the housing 88 through the rotational bearings 134. The drum has an extension 105 that extends away from the handle toward the housing. The outer circumference of this extension is secured to the inner circumference of the bearings 134, the outer circumference of which is, in turn, secured to the housing. Thus, the outer shaft 24 is translationally fixed relative to the housing, but may rotate relative thereto. Use of the extension insures rotational strength and rigidity, and minimizes total part count. Retaining rings are applied to the drum extension 105 on either side of the bearing pair to provide constraint and force resistance along the axis of the shaft. One 99 is shown near the bottom of the extension.

Figure 14:
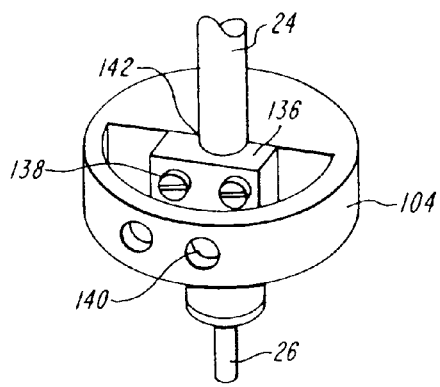
FIG. 14 shows schematically a perspective view of a rotary action drum of a linear capstan embodiment of the present invention.

The outer shaft 24 is secured to the coupling drum 104 by any suitable means. A preferred suitable means is shown in FIG. 14. It is beneficial to make the design as compact as possible along the tool length z dimension, which, is essential to maximization of the insertion range of motion. An effective way to do this is to embed the clamp into the drum 104.

In general, the drum 104 is partially hollow, with a separate flexure piece 136 clamped around the outer shaft 24 by two screws 138 threaded into the drum 104. These only need to be loosened slightly to accept or release the shaft 24. Thus, the clamp-piece 136 can remain attached to the drum 104 at all times during use. The drum 104 and clamp-piece 136 together form a circular cavity 142 (minus clearance for the clamping function). Access holes 140 permit direct screwdriver access to the screws 138. The terminal 1/16" (1.6 mm) of the coupling shaft in the drum extension 105 accommodates only the thinner, inner shaft 26 of the tool, so that a hard stop (not visible) is provided against which the end of the outer shaft 24 is pushed, to the proper reference position. Again, these screws 138 have the same interface as does the screw 130 that secures the inner shaft 26.

Cabling this axis is for a pure rotary transmission. As shown in FIGS. 13 and 15, a 0.25" (0.635 mm) diameter capstan 100 is used with a 1.13" (2.9 mm) diameter drum 104, to provide a 4.52:1 reduction. This brings the rotation axis motor 96 close to the housing 88, saving space and minimizing the cantilever effect on the motor mounting bracket 98. An extension 150 (shown only in FIG. 13) to the mounting plate 98 provides additional support for the capstan 100 of the rotation motor 96. This prevents the capstan 100 from tipping toward the drum 104, under the cable tension and the attendant damage from increased friction. As in the case with the jaw actuator, care must be taken to accurately locate a bearing 152 in the mounting plate extension 150, because the rotor is over-constrained.

Four wraps secure the cable 102 to the capstan 100. The cable ends 144a and 144b are anchored on the drum 104 to allow nearly 360° of travel, even though the required travel is only 180°, to provide greater versatility. In this case, the capstan 100 would undergo just over four rotations, meaning that the cable 102 would walk about four thread widths along the capstan. A standard but more compact (than on the jaw axis) 1/428 thread (26.45 per 6 mm) is used to save vertical space. The tensioning mechanism 146 for the rotary axis cable 102 is essentially identical to the one for the jaw axis and is placed inside the drum to maximize the travel available for drawing in the cable. The cable is attached lower on the drum for tensioning so that the tensioning mechanism could be more compact and so that the cable would not impose a large moment that would tend to tip the tensioning block.

Flanges 148 at the rim of the cable pathway around the drum 104 prevent accidental slipping of the cable off of the drum. Both angles of entry of the cable ends 144a and 144b to the drum are greater than ninety degrees, to prevent any sharp cable bends. The entrance holes are chamfered to further improve the conditions for the cable.

For some applications, the design shown may result in a rotary axis having less than optimal rigidity. For instance, when significant tension is applied to the cable, the drum 104 may tilt slightly toward the capstan 100. This may be due to any slight oversizing of the hole for the pair of bearings 134, which support the shaft and possibly to the material properties e.g. flexibility of the housing 88 (which may be made of ABS, for example). This slight compliance may also contribute to any discontinuity felt in the rotary axis. If further stiffness is required, the spread between the supporting bearings 134 can be increased, but this has the drawback of increasing the size along the shaft (z dimension). Alternatively, the housing 88 can be designed to support one bearing on each side of the drum 104. However, such a housing might need to be made in two pieces to insert the drum-coupling. This redesign could also incur some stiffness reduction, suggesting that the benefit may be limited. It would further undesireably increase device weight/volume and design complexity.

Transmission and Performance Consideration

Backdrive Friction and Backlash

For haptic devices in general, it is important to minimize the forces opposing backdriving the system by the user's motions. The forces result from friction and inertia in the device, which are scaled by the transmission ratio squared, when reflected to the user. The forces also arise from the transmission itself. These forces will be felt in addition to the simulated forces displayed, and will be present when the user is moving in simulated "free space," i.e., under simulated zero force conditions. For generalized haptic devices like the PHANTOM™ haptic interface, it is desired to reduce backdrive friction to as close to zero as possible, for all axes.

Because the present invention includes as an integral part an actual, non-ideal, lossy (friction, backlash) MIS tool handle and shafts, this requirement is not as stringent. In actual surgery, the cannula is able to pitch and yaw freely within the constraints of the body wall. Regarding the insertion, z axis, a fair amount of friction is associated with the insertion axis, however, due to the sliding of the tool shaft against the seal in the cannula both along the z axis, and around it. Since a realistic setup is required, this friction should be present as a consequence of using an actual trocar cannula and tool, and additional friction should be avoided.

Regarding the jaw action, detectable friction is contributed by the linkage, which drives the end effector in either grippers or scissors, and the sliding of curved surgical scissors blades on one another make an additional significant contribution.

Tests were performed to rate friction experienced at the handle in actual tools, bearing various end effectors. Scissors, which require 2.5 N, were characterized by dramatically greater friction than graspers, which required 0.4N. Removing the end effector and linkage completely (which is done to connect a typical handle to the handle module 84 of the present invention) results in markedly lower friction than either tool, presenting less than 0.001N. As a result, an actuation scheme that drives the inner shaft directly, as is done by the present invention, can have as much friction of its own as the lowest-friction tool, namely graspers, or about 0.4N.

Regarding rotation around the z axis, this experiences an amount of friction as well, due to the simple ball and socket in the handle and friction between the two shafts, but this is part of the handle, which is part of the final simulator. Consequently, additional friction in this axis should also be minimized unless the handle would be altered by some method to compensate.

Similarly, regarding backlash, in generalized haptic devices, it is desired for backlash in the system, as perceived by both the servo loop and by the user, to be zero. The latter constraint, that backlash between the position measured by the system sensors and the actuators be zero, is very important for the present invention as well. Backlash can cause instability in the servo loop because of: the force non-linearity caused by the delay in actuator engagement; and the discrepancy between measured and actual position. The implications of this constraint are that backlash in the transmission between the motor and the measured position should be minimal. However, a large amount of backlash is present in the lever and rotary dial mechanisms in the handle of actual MIS tools. There is 0.4 mm play in a typical gripper shaft travel, and 28° of play in a typical rotation dial. This backlash is apparent only to the user; it can and in fact should be left as is, since the surgeon's own internal "servo system" must be trained to compensate for this backlash.

Weight and Inertia

The mechanisms and actuators to be attached to the MIS tool handle to provide force feedback would clearly contribute a significant amount of weight and inertia to the tool. Having these be apparent to the user not only detracts from the realism of the simulation, but can contribute to muscle fatigue, particularly if the user must apply a constant force to support the weight of the device. If the simulator did add to the weight of the tool, then gravity compensation, or the application of a constant force equal to the additional weight in the vertical direction, could be implemented in software, or the weight could be physically counterbalanced in some manner. Neither solution is ideal; gravity compensation requires constant effort from one or more actuators, and may require that the compensating actuator be more powerful than otherwise necessary. Counterbalancing the weight contributes to the inertia of the system. Neither method can compensate for the apparent increase in inertia. Thus, in general, the gripper module of the invention should have minimal weight. This goal is generally consistent with a second requirement, that the inertia of the elements in each individual transmission be minimized to prevent excessive reflected inertia in any actuated axis. Thus, weight and inertia of the handle module should be minimized.

The present invention takes advantage of the fact that with the type of handle used, with its ball and socket joint, when the outer shaft rotates, the inner shaft does not, if there is no end effector joining their end-effector end. Thus, when the user rotates the outer shaft (either by rotating the wheel, or a wheel and the handles) the only parts that need to rotate with the outer shaft are the drum 104 and the capstan 100 of the rotary axis motor 96. The jaw action motor 92, the cartridge 90, and the housing 88, do not rotate. Thus, their rotary inertia is decoupled from rotation around the z axis. This minimizes any deleterious effect that might arise from the jaw axis actuation components. Their weight is still a factor to the other three DOFs. Thus, the fact that the jaw axis motor 92 is not oriented to minimize rotary inertia, is not as undesirable as it might seem, upon first thought.

Simulation

In a typical simulation, the mechanical interface, including the base, the PHANTOM™, or equivalent mechanical linkage, and the handle module, is situated so that it is out of view from the trainee/user, hidden from view by a synthetic body surface of the type under study. The trocar may be inserted in the true medical fashion (using the trocar cutting blade) through this synthetic body material, or, through holes provided, or through simulated natural orifices, depending on the type of body simulator. The synthetic body is then covered in a traditional drape configuration. The extension tube is then inserted into the trocar, as would be an actual tool and the handle remains outside to be manipulated by the user. The only difference is that the distal end of the simulator extension tube carries no end effector.

At this point, the simulation departs from reality, as the inner shaft 26 and outer shaft 24 are inserted into and secured to the cartridge 90 and drum 104, respectively. Afterwards., the simulation is rejoined, as the mechanical interface, including a base mechanical interface 50, such as a modified PHANTOM™ or Martin '197 type linkage, and a handle module, and handles, all under control of the software controller, presents forces to the user. Ideally, the forces are identical to those as if the user were manipulating an MIS handle and tube and were encountering internal body parts of a patient. Simultaneously, the visual display is provided with images that correspond to an internal surgical environment. For instance, the controller may be configured to actuate the first actuator to present forces to a user engaging the contact members that are proportional to their relative velocity, thereby simulating a damping factor relative to their motion, or their relative displacement, thereby simulating an elastic spring factor.

A simple demonstration program was developed to validate the hardware disclosed here. It was based on a large, compliant haptic sphere (stiffness of 0.1N/mm, typical of some organs) rendered by a PHANTOM™ mechanical interface, with which a gripper tool tip, modeled visually by a small sphere, could interact. When the user pushed the tool into the sphere, spring-modeled force was applied to the gripper axis and twist axis in both directions. Therefore, the user felt resistance upon closing the gripper on the "tissue" as well as when attempting to spread the gripper inside it, analogously to the use of this tool to spread tissue, as is commonly done. Furthermore, the user was able to grip the tissue and pull out of the sphere, feeling it pull back and feeling resistance upon trying to twist as well. Finally, if the user then released with the gripper, this force was terminated, generating the sensation of the tissue "snapping back". At all times, "gravity compensation" was implemented; that is, a constant vertical force was applied by the PHANTOM™ haptic base 50 equal in magnitude to the weight of the handle module and other parts of the mechanical interface, so that the user did not feel that the tool bore any additional weight, other than a normal laparoscopic tool.

The graphical display was relatively simple and performed in Open Inventor available from Silicon Graphics Incorporated of Mountain View, Calif.

Surgeon analysis of the apparatus described above is favorable. The magnitudes of the applied forces and torques as well as the available range of motion for all axes, are adequate.

The foregoing tests were conducted using as a mechanical base 50 a PHANTOM™ 1.0 SW (Standard Workspace) haptic interface, as manufactured and a 6 axis amplifier card and box, or 2–3 axis cards and boxes. Each axis of the handle module 84 was wired identically to the PHANTOM™ axis configuration for the sake of consistency. During simulation use, one 52a of the two motors driving the parallelogram linkage on the PHANTOM™ became very warm. This motor carried most of the continuous load of providing the gravity compensation. Thus, although the altered handle 18 and the handle module 84 weighed only 0.37 pounds, while the PHANTOM™ interface maximum force output was specified at 1.9 pounds, applying the smaller load on only one motor relatively continuously drew enough current that in continuous operation this motor could overheat. A proposed solution is to add a further counterweight to the PHANTOM™ interface, so that the device with the handle module and a handle is balanced in a set, home position and software gravity compensation is unnecessary for the set position. There would be a tradeoff involved, however, in the form of a possibly discernable increase in inertia on the three primary axes of motion. It might also be possible to tip the base mechanical interface 50 so that both of the motors 52a and 52b help support the weight. A further alternative would be to alter the control routines for the PHANTOM™ interface, as it is generally optimized for general applications. This optimization might not be the most suitable for the weight carrying application disclosed herein.

The tests were conducted using PHANTOM™ I/O libraries. In any particular commercial product there would be a specific, efficient way of accomplishing control, based on the specific specifications. One of skill in the art would be able to program the device, using general principals of haptic control such as discussed in (Burdea, 1996) and documentation that is provided by Sensable Technologies, Inc. and Immersion Corp. with their devices.

Significant effort is required to simulate the MIS environment in which the MIS tool operates. Many researchers are working on this project. Such simulation would be conducted by programming the base portion of the mechanical interface, and the handle module portion of the mechanical interface to present the forces that a particular model of the environment calls for. At present, it is rather routine to program the interface to present the forces, if the forces are known. Much work is being conducted to determine what the forces should be.

As has been mentioned, if a PHANTOM™ interface is used for the base mechanical interface 50, it is convenient to use a second PHANTOM™ control card and amplifier box to control the additional gripper module device axes. This second controller card executed closed-loop PID control on the motor current, which directly commanded the output torque. Conversions based on each transmission ratio and the torque constant of the motors were used to calculate the current corresponding to the force or torque desired for display to the user; these conversions are given in the following table.

| | Encoder Count to Position Conversion | Output Force/Torque to Input Motor Current Conversions |
|---|---|---|
| Jaw Action | 0.0164 mm/count | 0.1 A/N |
| Rotation Action | 0.36 degrees/count | 0174 A/Nm |

Other Mechanical Interface Platforms

Figure 6:
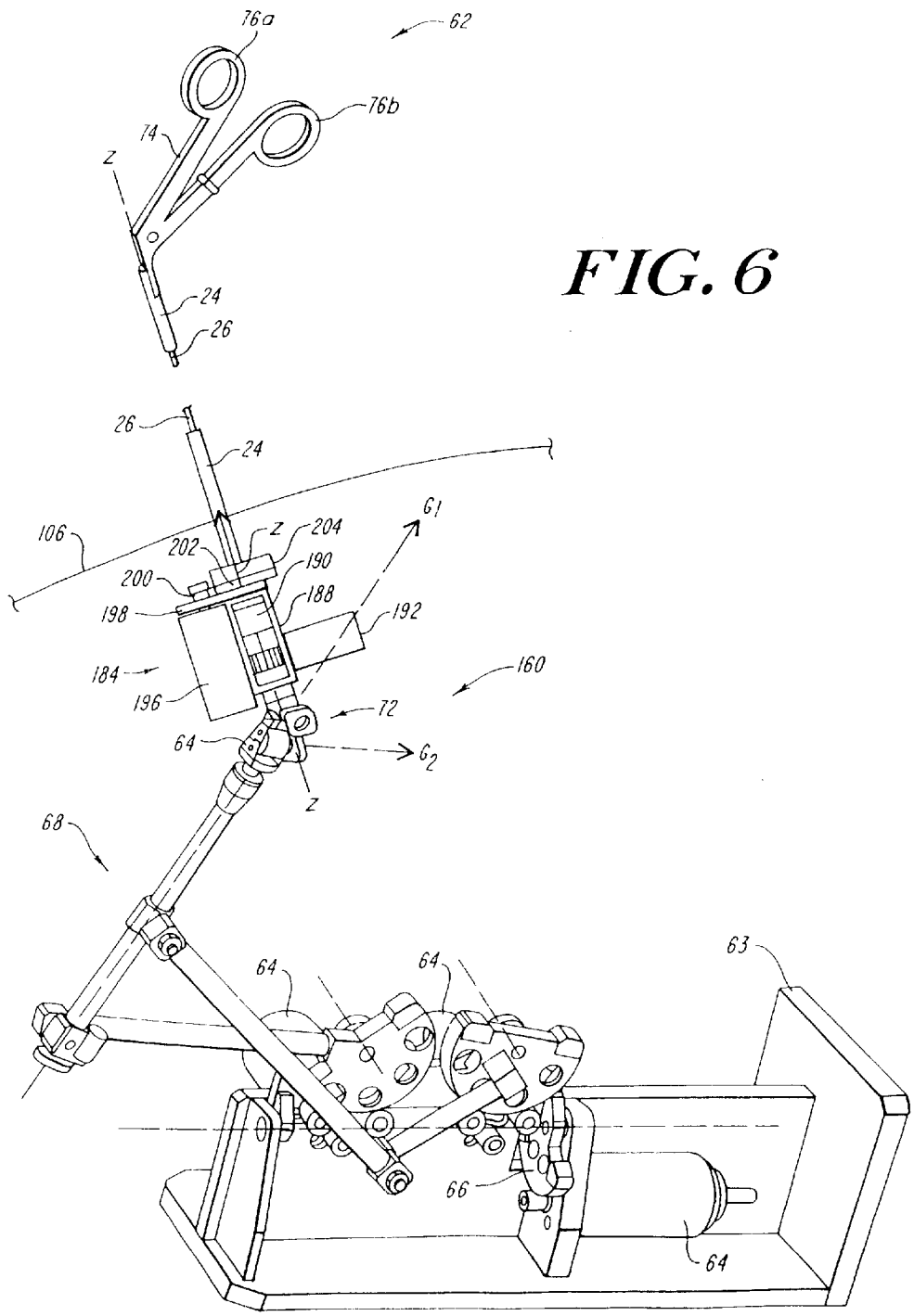
FIG. 6 shows schematically an embodiment of the present invention using a Martin '197 patent type base mechanical interface and a linear capstan handle module.

The foregoing has described using a PHANTOM™ type haptic interface as part of the mechanical interface 46. It is also possible to use a Martin '197 type device as the base 160 part of the mechanical interface 46, as shown schematically with reference to FIG. 6. In that embodiment of the invention, the handle module 184 is shown schematically. However, it may be essentially identical to that discussed above with reference numerals increased by one hundred. It would be used in the same manner.

The PHANTOM™ and the Martin '197 interface devices actuate at a tip. They may both also be thought of as open chain, or serial devices. In other words, the point of interaction with the user is the end of a chain or series of links and joints that are connected to each other, end to end. These were chosen as most useful, at the time of invention, for simulation, because they can be most readily hidden within or below a synthetic torso, as shown and explained above. There is another general class of mechanical interfaces, which actuate around the pivot point. They may be thought of as closed chain, or parallel devices, of which the Immersion Impulse Engine and the force feedback Device developed by the Bleuler Lab of Ecole Polytechnique are examples.

The presently described handle module can be used with either the tip actuated devices, as described, or a pivot actuated device. It would, in that case, be beneficial to use a version of the device, that has its housing configuration and actuator layout modified to fit within the apparatus of whichever device is used.

A tradeoff exists between tip- and pivot-actuated devices regarding kinematics: tip-actuated devices keep all hardware well below the body wall pivot point, making it possible to bring trocars closer together, offering better compatibility with synthetic torso models, and allowing a larger range of motion for the pitch/yaw (x, y) and insertion (z) axes. However, because the pivot-actuating devices keep the tool tip completely free of additional hardware, it would theoretically be possible for the tips of two instruments to interact much more closely, in which the bulk of the hardware lay to one side. Furthermore, some pivot actuated devices ground as many motors as possible, since motors that travel with one or more axes contribute to the perceptible inertia of these axes. As a beneficial corollary, actuators fixed to ground could be chosen to be as powerful as needed, facilitating higher maximum forces and torques.

A second distinction exists regarding dynamics considerations. Higher stiffness can be offered by the pivot actuated devices over the tip actuated ones. Typically, however, this would be perceptible mainly in representing rigid objects far stiffer than human tissue. Since these objects, namely bone and other tools, are typically simulated predominantly as placeholders to indicate errors in the user's trajectory, rather than for extended engagement and palpation, it is not a concern to be able to represent these items with a high degree of verisimilitude.

The actuation paradigm of the tip-actuating designs is somewhat cleaner and more elegant. The device actually becomes the tissue, resisting with the same forces that the tissue models calculate. In the pivot-actuating models, the torque to be applied to the tool shaft would be not only a function of the interaction of the virtual tool tip and tissue, but also of the distance of the tool tip from the fulcrum, Tip-actuation offers greater compatibility with a more realistic external environment and compliant body wall, and more flexibility in repositioning for different trocar ports. Pivot-actuation provides the convenience of holding the receptacle for the tool near the trocar, making reinsertion of the tool more straightforward. However, it is difficult (if not impossible) to provide insertion force feedback without adding a cable along the length of the tool, which would compromise visual integrity, or without using rollers, compromising bandwidth by the addition of friction and compliance.

The conclusion from the above considerations is that a tip actuated device such as suggested by the Martin '197 patent or the PHANTOM™ interface provides the best platform of known devices.

The foregoing has generally described using the handle module and base mechanical interface as part of a master to interact with a virtual environment. Such a use is particularly advantageous for simulating MIS activities, for instance for training, or for planning an operation, as discussed above. Such a use also facilitates quantitatively evaluating trainees, performance, as it is a relatively routine matter to track the motions, and the forces, store them in memory, and map them to the virtual environment to determine whether the virtual surgeon has accomplished the surgical goals and how efficiently or proficiently, or has caused surgical damage. Thus, it achieves the objectives of providing a useful training and evaluation tool.

Use as a Master Device, with a Slave Device

Figure 18:
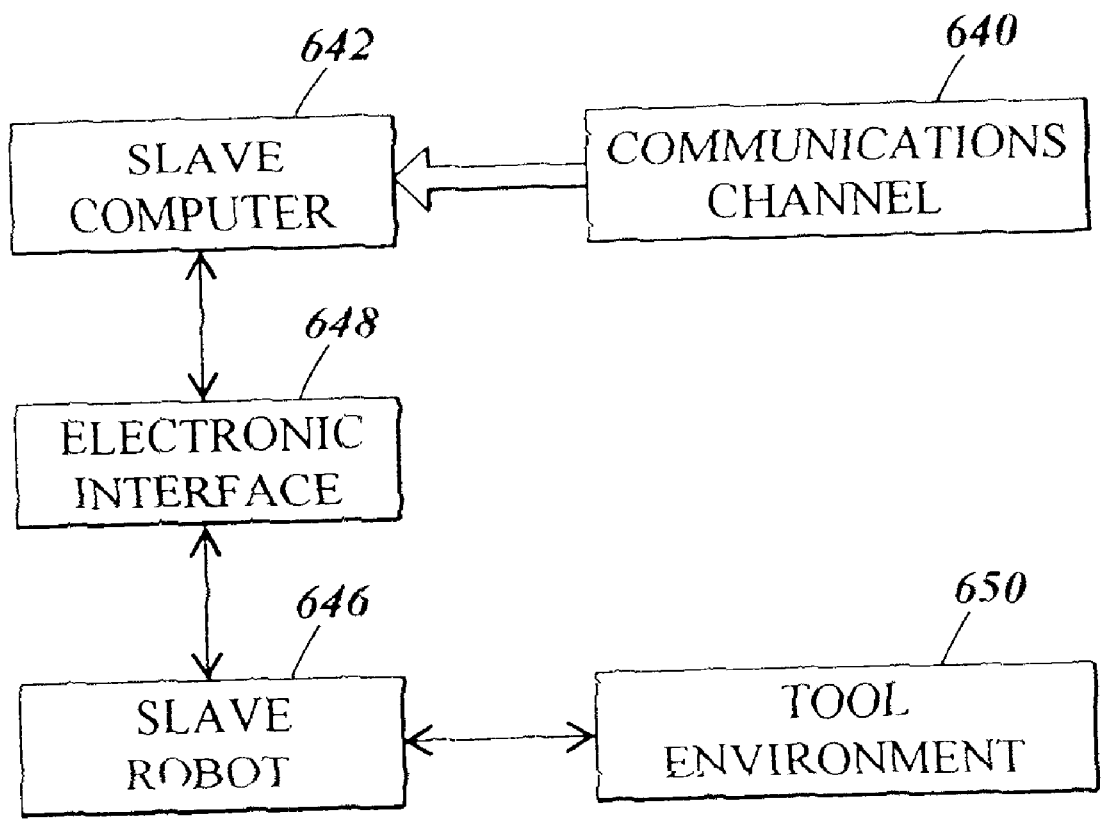
FIG. 18 shows schematically a telerobotic embodiment of the present invention.

The handle module and base mechanical interface may also constitute a master to interact with a slave robot that operates on a subject in a slave environment. The slave environment may be distant, such as in a teleoperation system, for instance on a battlefield, or immediate, such as in a robotic assisted operation, where the robotic system amplifies the surgeon's senses of touch and motion control. Thus, the handle module and base mechanical interface can be used as part of a master slave system. For instance as shown schematically with reference to FIG. 18, it could be used as a master to control any of the slave devices disclosed in the four patent documents by Madhani, identified above. It can be used to control any slave device 646 that has a jawed actuator, such as a gripper, and that moves with up to the five DOFs discussed (z translation, x, y and z rotation, and gripping). It can also be used to control single element (non-jawed) devices. Further, it can even be used to control devices having more than 5 DOFs, according to the methods discussed in the Madhani PCT ROBOTIC APPARATUS document, PCT/US98/19508.

Thus, the apparatus of the invention is suitable for use as a master that interacts with any sort of tool environment, either virtual, such as in a simulation, or real 650, such as as part of a master/slave system. As used herein, a "tool environment" shall include any environment, either tangible and physical, or virtual and simulated by a computer system, that corresponds to a tool, moving in an environment. A first example is a software environment, existing in a software representation embodied in a programmed computer, either general purpose or specially dedicated. Such a virtual environment includes a representation of a tool that has properties, such as size, in one, two or three dimensions, mass, inertia surface properties, such as hardness, body characteristics, such as elasticity, etc. The representation also includes an environment in which the tool resides and moves, which environment may include boundaries, internal structures, for instance that represent organs of a medical subject, and rules for the motion of the tool within the environment, which may have to do with reasonable position, velocity and acceleration of the tool.

A second example is a physical, tangible environment, that includes a physical, tangible tool 646, that is actuated by actuators, such as motors, under control of a computer controller 642. The tool is physical, and resides in a physical tool environment 650. Such a tool can be a surgical tool used as a slave robot, under control of a master input device. The slave can be located distant from the master, such as in a teleoperation upon a real patient, or, it can be relatively nearby, such as in a master/slave enhanced surgery application. The master computer 42 unit communicates with the slave computer 642 through a communications channel 640.

Fewer DOFs

The handle module described above actuates both jaw action such as gripping or scissoring, and rotation around the z axis, basically along the tool shaft. There are some situations where only one of these degrees of freedom is necessary. Eliminating the apparatus to actuate the other degree of freedom would significantly reduce the weight and inertia of the gripper module (in general, by about one-half). Thus, for some dedicated applications, such limited DOF embodiments may be very useful.

For instance, if it is desired to actuate only the jaw DOF, because, for instance, it has been determined that the forces resulting from rotation are so slight as to not warrant the extra equipment, then a jaw module can be used that has only the single actuator 92, the housing 88 and the cartridge 90 that slides therein. There would be no need for the second actuator 96, or the drum 104 that makes up the transmission for the rotary axis actuation. It would also be convenient to use an essentially standard three DOF gimbal, and to eliminate the drum 104.

Conversely, if it is desired to actuate only the rotary action, because, for instance, the tool that is being simulated has no jaw capability, for instance it being a simple blade, then a tool module (it would not be appropriate to refer to it as a jaw module) can be used that has only the single actuator 96, and the drum 104 that makes up the transmission for the rotary axis actuation. Other non-jaw tools include: blunt probes, dissectors and scalpels.

Applications other than MIS

The foregoing discussion has focussed on using the apparatus of the invention as part of a user input device for MIS uses. However, it is suitable as a user input device for any use that involves a tool environment having jaws, such as grippers or scissors, and/or rotation around a tool axis. Thus, the tool environment, either virtual or actual, as explained above, could be a non-surgical one in which hazardous materials, such as radioactive fuel is manipulated. Or, it could be an environment that is hazardous for human occupation, such as under water, outer space, under ground, for instance in mines, etc. The apparatus could also be used as part of a master for construction or demolition equipment, such as demolition claws, or lumber lifting jaws.

Variations of Actuating Gripper and Rotation Axes

Other specific embodiments for actuating the gripper and rotation axes are also possible. Two representative embodiments are shown schematically with reference to FIG. 16, which shows an arc-section cable drive embodiment, and FIG. 17, which shows a ballscrew embodiment.

Turning first to the arc-section cable embodiment, FIG. 16 shows a simplified version of such an apparatus. An outer shaft 324 of a tool, analogous to the outer shaft 24, is fixed, rotationally and translationally, to a housing 388. The housing is, in turn, connected through a rotational bearing 397 to a gimbal arm 382, which is the terminal link of a gimbal that is part of a base mechanical interface, such as a PHANTOM™ device, as described above. A motor 396 stator is fixed to the gimbal arm and its rotor arm is coupled to the housing, so that they rotate together, perhaps with some transmission interposed. An inner shaft 326 is coupled to a section of an arc 390 through a ball joint 327. The arc section is pivotably coupled to the housing 388 through a pivot joint 389. The arc section 390 is coupled through a cable 394 to the capstan 314 of a jaw action actuator 392, the stator of which is fixed relative to the housing 388. The outer shaft 324 is concentric to the motor 396.

Figure 7:
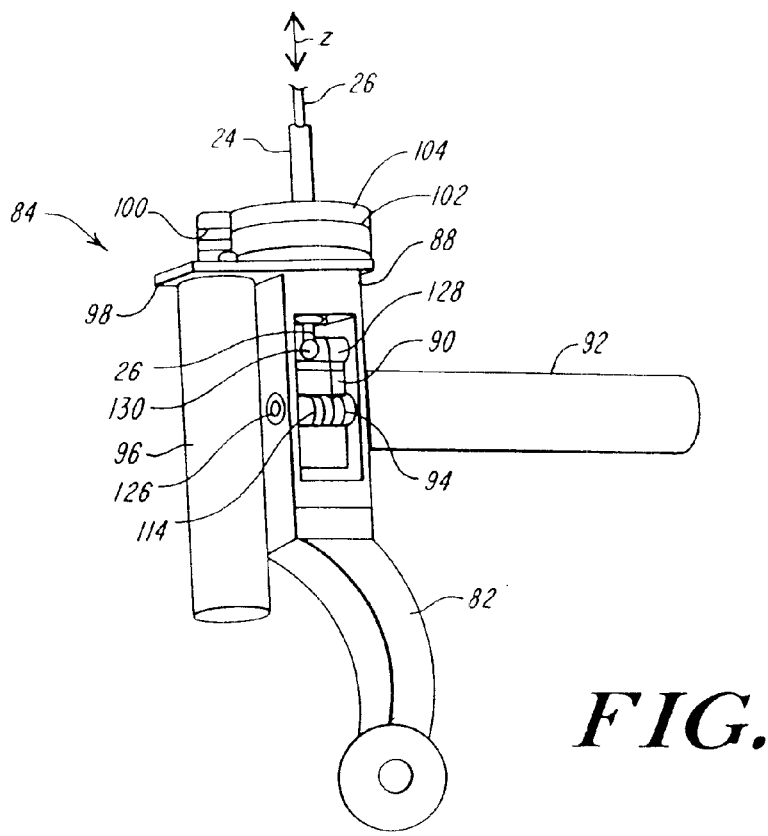
FIG. 7 shows schematically an embodiment of the present invention using a linear capstan to actuate the jaw action of the handle module.

Relative translation between the inner and outer shafts causes rotation of the arc-section. Thus, the jaw action is actuated through the motor 392, and the rotary action is actuated through the motor 396. Handle closing/opening backdrives the jaw action motor 392 and handle rotation backdrives the rotation motor 396. Advantages of the arc-section embodiment, as compared to the linear capstan embodiment shown in FIG. 7, are that the arc-section provides reduction without gears, and has no linear bearings or sliding surfaces. Disadvantages are that it is governed by a non-linear force relationship. Further, to generate enough torque using reasonably small motors, requires a relatively large arc section, and thus a relatively large device and large rotations inertia.

Turning next to the ballscrew embodiment, FIG. 17 shows a simplified version of such an apparatus, in partial cross-section. An outer shaft 424 of a tool, analogous to the outer shaft 24, is fixed to a housing 488. Thus, they rotate and translate together. The housing is, in turn, coupled through bearings 434 to a gimbal arm 482, which is the terminal link of a gimbal that is part of a mechanical interface, such as a PHANTOM™ device, as described above. The housing 488 can rotate about the z axis relative to the gimbal arm 482. An inner shaft 426 is fixed to a cartridge 490 through a ball joint 427. It is not necessary that this joint be rotational, and, rather than a ball joint, a simple clamp, or flexure could be used. The cartridge 490 is translationally coupled to the housing 488 through sliding surfaces 489 or a linear bearing. (For simplicity, the space where the sliding surface would be is shown empty.) The cartridge 490 is coupled through a leadscrew 494 to the rotor 414 of a jaw action actuator 492, the stator of which is fixed relative to the housing 488. The outer shaft 424 is fixed to the housing 488, which has an integral drum 404. This drum is driven by the motor 496, the stator of which is fixed to the gimbal link 482.

Relative translation between the inner and outer shafts causes relative translation between the housing 488 and the cartridge 490 and vice-versa. Thus, the jaw action is actuated through the motor 492, and the rotary action is actuated through the motor 496. Handle closing/opening backdrives the jaw action motor 492 and handle rotation backdrives the rotation motor 496. Advantages of the ballscrew embodiment, as compared to the linear capstan embodiment shown in FIG. 7, are that the ballscrew embodiment has less rotational inertia. However, as discussed above, this is not very important. Disadvantages are that it is more complicated and costly to build, less robust, and has more linear backlash and more resistance to gripper action backdriveability.

Variations

The foregoing has illustrated the invention with jawed tools having two jaws. However, it may also be used with jawed tools that have more than two jaws, if the tool is actuated by a handle with two or more moving members. For instance, it can be used with an instrument that has several jaws that are attached to a collar, which is closed by retraction of the collar and jaws into a narrow sleeve.

The foregoing has illustrated the invention with a handle that has a wheel, which decouples the rotation of the shafts from the handles. This is a very common feature of handles, and as such, it is faithful to reality if the simulator includes such a wheeled handle arrangement. However, some handles do not include such a wheel, in which case, the outer shaft rotates with the handles. If such a tool is to be simulated, then the handle actuator of the invention can be made with such a handle, in which case, rotation of the outer shaft must be accomplished by rotation of the handles. What is required for the invention is that when there is no end effector on the shafts, the inner and outer shafts should be decoupled rotationally. Further, the inner shaft must be attached to the handles so that rotation of the handles does not cause rotation of the inner shaft, if there is no end effector attached to the shafts. Thus, the mechanism that actuates the jaw action is decoupled from the rotation of the handles and the outer shaft, and does not rotate when the handles are rotated. This is an important design feature of the present invention.

The foregoing has illustrated the invention using rotary motors. However, other types of actuators may be used, including pneumatic devices and linear motors. Also, it will be understood that although rotor and stator have been used, these terms are defined herein and in the claims to also mean the corresponding moving and stationary parts of linear motors and pneumatic devices, as they are conventionally regarded.

The foregoing has focussed generally on a tool having a pair of loop type handles as the user contact members. However, the user contact element may be any configuration suitable for opening and closing jaws, such as, a linear syringe-type configuration, with a plunger, having a loop or flat handle, and one or two finger engaging elements, such as loops or overhangs.

Further, although the foregoing has mentioned that the handles of a conventional MIS tool rotate relative to each other, which they do, there are also parts of the handles that may be considered to translate relative to each other, for instance, the loops, and thus, their function could be performed by two components that translate relative to each other, rather than rotate, such as the two elements of a syringe (plunger and vessel).

The foregoing has focussed generally on a tool sized to be used by a human hand. However, the invention can also be used with different sized tools, including but not limited to those sized to be engaged by two human feet, rather than two human fingers , for instance using pedals or foot clips , or two human arms, for instance using larger handles, one for each hand.

Thus, to summarize, there are many aspects of the invention. One aspect is a tool actuation module that can be added to a base mechanical interface, such as a PHANTOM™ haptic interface, or a Martin '197 type interface. The tool actuation module can be one that actuates both jaw action and rotation around the tool axis, or one that actuates only one of these two degrees of freedom. Another aspect of the invention is a mechanical user interface that includes both the tool actuation module, according to any of the embodiments mentioned above, in combination with a base mechanical interface, such as a PHANTOM™ haptic interface, or a Martin '197 type interface. Such a combined device may be used as a user interface for a simulator, such as an MIS simulator, or a master robot in a telerobotic system. Yet another aspect of the invention is a simulator, using the tool actuation module and base mechanical interface combination, as discussed above, in further combination with a virtual environment simulator, such as a properly programmed general or special purpose computer. Still another aspect of the invention is a telerobotic system, including a master robot that comprises a tool actuation module in combination with a base mechanical interface, as explained above, a communications channel, and a slave robot and controller located in a different environment.

The foregoing discussion should be understood as illustrative and should not be considered to be limiting in any sense. While this invention has been particularly shown and described with references to preferred embodiments thereof, it will be understood by those skilled in the art that various changes in form and details may be made therein without departing from the spirit and scope of the invention as defined by the claims.

The corresponding structures, materials, acts and equivalents of all means or step plus function elements in the claims below are intended to include any structure, material, or acts for performing the functions in combination with other claimed elements as specifically claimed.

The following literature may be of interest to the practitioner.

Burdea, G. (1996). Force and Touch Feedback for Virtual Reality. John Wiley and Sons.

Gorman, P. J., Lieser, J. D., Murray, W. B., Haluck, R. S., and Krummel, T. M. (1999). Evaluation of Skill Acquisition Using a Force Feedback, Virtual Reality Based Surgical Trainer. *Medicine Meets Virtual Reality*, 121–123.

Hunter, I. W., Jones, L. A., Sagar, M. A., LaFontaine, S. R., and Hunter, P. J. (1995). Opthalmic microsurgical robot and Associated Virtual Environment. *Computers in Biology and Medicine*, 25(2):172–182.

Madhani, A. (1998) Design of Teleoperated Surgical Instruments for Minimally Invasive Surgery. Doctoral Thesis, Department of Mechanical Engineering, MIT.

Massie, T. H. and Salisbury, J. K. (1994). The Phantom Haptic Interface: A Device for Probing Virtual Objects. *Dynamic Systems and Control*, pages 295–299.

Vollenweider, Marc. (Aug. 6, 1999). "Project Simulator for Laparoscopic Surgery". Ecole Polytechnique, Bleuler Laboratory. http://dmtwww.epfl.ch/isr/mmt/biomed/

Having described the invention, what is claimed is:

1. A haptic apparatus to interface a human user with a tool environment through the interchange of force, the apparatus comprising:
   a. a user contact element for physically contacting a body member of the user, the contact element comprising a pair of first and second contact members that are movable relative to each other;
   b. a first elongated member that is translatably fixed to the first contact member;
   c. a second elongated member that is parallel with the first elongated member, and that is coupled to the second contact member, such that the second elongated member is translatable relative to the first elongated member upon relative motion of the first and second contact members, the second elongated member further being rotatable relative to the first elongated member upon rotation of the first contact member relative to the second elongated member;
   d. a first actuator, which is coupled to both of the first and second elongated members, such that upon actuation the first actuator actuates relative translation of the first and second elongated members; and
   e. a second actuator, which is coupled to both of the elongated members, such that upon actuation, the second actuator actuates relative rotation of the first and second elongated members about an axis parallel to their axes of elongation.

2. The apparatus of claim 1, the first and second elongated members comprising substantially concentric shafts, the first being a hollow outer shaft that surrounds the second, which is thus an inner shaft.

3. The apparatus of claim 2, the contact element comprising a two handled element, with the first and second contact members constituting the handles, being rotatable relative to each other about an axis that is perpendicular to the axis of elongation of the first and second shafts.

4. The apparatus of claim 2, the contact element comprising a two handled element, with the first and second contact members constituting the handles, being translatable relative to each other.

5. The apparatus of claim 2, the contact element comprising a two-handled minimally invasive surgery handpiece.

6. The apparatus of claim 5, the first contact member comprising a loop handle that is fixed to the first elongated member.

7. The apparatus of claim 5, the first contact member comprising a wheel that is fixed to the first elongated member, and that is coupled to a loop handle such that the wheel is rotatable around an axis that is parallel to the axis of elongation of the first elongated member, relative to the loop handle, and fixed translationally relative to the loop handle, such that the first elongated member is rotatable relative to the second contact member and the loop handle of the first contact member by rotating the wheel about its axis of rotation.

8. The apparatus of claim 2, each actuator having a nominally stationary part and a nominally movable part, the apparatus further comprising a housing, to which the stationary part of both actuators are attached, the outer elongated member being rotatably coupled and translatably fixed to the housing and the inner elongated member being rotatably fixed and translatably coupled to the housing.

9. The apparatus of claim 8, the first actuator comprising a rotary motor, having a stator and a rotor, wherein the rotor is coupled to the inner elongated member such that actuation of the first actuator actuates relative translation between the inner elongated member and the housing, and thus, between the inner and the outer elongated members.

10. The apparatus of claim 9, wherein the coupling between the rotor of the first actuator and the inner elongated member comprises a cable transmission.

11. The apparatus of claim 10, wherein the cable transmission comprises a cartridge that is fixed to the inner elongated member, and that is translatably coupled to slide along an axis, relative to the housing, and that is coupled by the cable transmission to the first actuator.

12. The apparatus of claim 11, the axis along which the cartridge is slidable being substantially parallel to the axis of elongation of the elongated members.

13. The apparatus of claim 9, the first actuator having a first rotor axis, and being arranged with the first rotor axis substantially perpendicular to the first elongated member.

14. The apparatus of claim 8, the second actuator comprising a rotary motor, having a second stator and a second rotor, wherein the second rotor is coupled to the outer elongated member, such that the second actuator actuates relative rotation between the outer elongated member and the housing, and thus between the outer elongated member and the inner elongated member.

15. The apparatus of claim 14, the coupling between the second rotor and the outer elongated member comprising a cable transmission, that comprises a cable and a drum.

16. The apparatus of claim 14, the second actuator having a rotor axis, and being arranged with its rotor axis substantially parallel to the first elongated member.

17. The apparatus of claim 14, the first and second actuators each having a rotor axis, and being arranged with their respective rotor axes substantially perpendicular to each other.

18. The apparatus of claim 8, further comprising a base mechanical interface unit that comprises:
  a. an interunit link that is fixed to the housing;
  b. a powered base linkage that couples the interunit link to a base foundation, with the interunit link being movable through at least five degrees of freedom relative to the base foundation, whereby the powered base linkage is arranged, upon activation, to actuate the interunit link and thus the housing, with respect to at least three degrees of freedom of motion relative to the base foundation.

19. The apparatus of claim 18, the powered base linkage comprising at least three actuators that are rigidly connected to the base foundation.

20. The apparatus of claim 18, the powered base linkage comprising at least three actuators, at least two of which are coupled movably to the base foundation, to act, in part as counterbalance for the linkage between the actuators and the interunit link.

21. The apparatus of claim 18, the powered base linkage comprising a tip actuated linkage.

22. The apparatus of claim 18, the powered base linkage comprising a pivot actuated linkage.

23. The apparatus of claim 1, further comprising a displacement sensor arranged upon activation to generate a signal that corresponds to the relative translational displacement between the first and second elongated members.

24. The apparatus of claim 1, further comprising a displacement sensor arranged upon activation to generate a signal that corresponds to the relative rotational displacement between the first and second elongated members.

25. The apparatus of claim 1, further comprising first and second displacement sensors arranged upon activation to sense the relative translational and rotational displacement, respectively, between the first and second elongated members, and to generate signals that correspond thereto, the first and second sensors being coupled to a controller that is coupled to the first and second actuators, the controller further arranged, upon activation, to control the first and second actuators based, in part, upon the signals from the displacement sensors.

26. The apparatus of claim 25, the controller configured to actuate the first actuator to present forces to a user engaging the contact members that simulate minimally invasive surgery tool jaws urged against a resisting force.

27. The apparatus of claim 26, the controller configured to actuate the first actuator to present forces to a user engaging the contact members that simulate minimally invasive surgery tool gripper jaws opening against a resisting force.

28. The apparatus of claim 26, the controller configured to actuate the first actuator to present forces to a user engaging the contact members that simulate minimally invasive surgery tool gripper jaws closing against a resisting force.

29. The apparatus of claim 26, the tool environment comprising a slave device that is configured to be operated by the haptic interface apparatus as a master device, the apparatus further comprising:
  a. a controller coupled to the slave device, configured upon activation to control its motions; and
  b. a communications channel, coupling the controller for the master device to the controller for the slave device.

30. The apparatus of claim 29, the slave robot comprising a minimally invasive surgery apparatus for use upon a subject, having an end effector with two actuated members that are movable relative to each other under actuated control, and which contact the subject in use.

31. The apparatus of claim 30, the actuated end effector members further being rotatable together around an axis under actuated control.

32. The apparatus of claim 30, the controller further configured to:
  a. receive signals through the communications channel from the slave device that correspond to any force that the actuated end effector members experience if and contacting the subject while actuated to move relative to each other; and
  b. actuate the first actuator to actuate relative rotation of the user contact members to present a force to a user in contact with the user contact members that corresponds to any such force that the end effector members experience upon moving relative to each other.

33. The apparatus of claim 30, the controller further configured to:
  a. receive signals from the communications channel from the slave robot that correspond to any force that the actuated end effector members experience if contacting the subject while actuated to rotate together; and
  b. actuate the second actuator to actuate rotation of the first elongated member relative to the second elongated member to present a force to a user in contact with the user contact element, which corresponds to any such force that the end effector members experience upon rotating together.

34. The apparatus of claim 25, the controller configured to actuate the first actuator to present forces to a user engaging the contact members that simulate minimally invasive surgery tool scissor jaws cutting through an object.

35. The apparatus of claim 25, the controller configured to actuate the first actuator to present forces to a user engaging the contact members that are proportional to their relative velocity, thereby simulating a damping factor relative to their motion.

36. The apparatus of claim 25, the controller configured to actuate the first actuator to present forces to a user engaging the contact members that are proportional to their displacement from a reference location, thereby simulating a spring factor relative to their displacement.

37. A haptic apparatus to interface a human user with a tool environment through the interchange of force, the apparatus comprising:
  a. a user contact element for physically contacting a body member of the user, the contact element comprising a two-handled minimally invasive surgery handpiece with a pair of first and second loop handles that are movable relative to each other;

b. a first, outer elongated member that is translationally fixed to the first loop handle;

c. a second, inner elongated member that is concentric with and inside the first elongated member, and that is coupled to the second loop handle, such that the inner elongated member is translatable relative to the outer elongated member upon relative motion of the two loop handles, the outer elongated member further being rotatable relative to the inner elongated member upon rotation of the first loop handle relative to the inner elongated member;

d. an actuator, having a stator and a rotor, which actuator is coupled to both of the outer and inner elongated members, such that upon actuation the actuator actuates relative translation of the inner and outer elongated members; and e. a housing, to which the stator is attached, the outer elongated member being rotatably coupled and translatably fixed to the housing and the inner elongated member being rotatably fixed and translatably coupled to the housing wherein the rotor is coupled to the inner elongated member such that actuation of the actuator actuates relative translation between the inner elongated member and the housing, and thus, between the inner and the outer elongated members.

38. The apparatus of claim 37, wherein the coupling between the rotor and the inner elongated member comprises a cable transmission having a cartridge that is fixed to the inner elongated member, and that is translationally coupled to slide along an axis, relative to the housing, the translation of the cartridge being actuated by the actuator.

39. The apparatus of claim 38, the actuator having a rotor axis, and being arranged with the rotor axis substantially perpendicular to the outer elongated member.

40. The apparatus of claim 39, further comprising a base mechanical interface unit that comprises:

a. an interunit link that is fixed to the housing;

b. a powered base linkage that couples the interunit link to a base foundation, with the interunit link being movable through at least six degrees of freedom relative to the base foundation, whereby the powered base linkage is arranged, upon activation, to actuate the interunit link and thus the housing, with respect to at least three degrees of freedom of motion relative to the base foundation.

41. The apparatus of claim 38, further comprising a displacement sensor arranged upon activation to sense the relative translational displacement between the first and second elongated members, and to generate signals that correspond thereto, the displacement sensor being coupled to a controller that is coupled to the actuator, the controller further arranged, upon activation, to control the actuator based, in part, upon the signal from the displacement sensor.

42. The apparatus of claim 41, the controller configured to actuate the actuator to present forces to a user engaging the loop handles that simulate minimally invasive surgery tool jaws urged against a resisting force.

43. A minimally invasive surgery simulator apparatus comprising:

a. a handle unit comprising:
   i. a pair of handles that correspond to handles of a minimally invasive tool;
   ii. a pair of parallel elongated members that have an axis of elongation, and that translate relative to each other along their axis of elongation and that rotate relative to each other around the axis of elongation, each being coupled to a respective one of the handles;

b. a handle actuation module comprising:
   i. a housing, the first elongated member being rotatably coupled and translatably fixed to the housing and the second elongated member being rotatably fixed and translatably coupled to the housing;
   ii. a backdrivable first actuator, the stator of which is coupled to the housing, and the moving part of which is coupled to the second elongated member, such that the first actuator actuates relative translation between the pair of elongated members;
   iii. a sensor that generates a signal that corresponds to translation displacement between the two elongated members;

c. a base mechanical interface unit comprising:
   i. a handle actuation module support, to which the housing is fixed;
   ii. a base foundation, coupled to the handle actuation module support, such that the handle actuation module is movable through at least three additional Degrees of Freedom relative to the base foundation;
   iii. a plurality of backdrivable actuators, coupled between the base foundation and the handle actuation module support, such that upon activation, the plurality of actuators actuates motion of the handle actuation module support relative to the base foundation; and
   iv. a sensor assembly that generates a signal that corresponds to displacement between the handle actuation module support and the base foundation, relative to the at least three additional Degrees of Freedom.

44. The apparatus of claim 43, the handle actuation module further comprising:

a. a backdrivable second actuator, the stator of which is coupled to the housing, and the moving part of which is coupled to the first elongated member, such that the second actuator actuates relative rotation between the pair of elongated members; and b. a sensor that generates a signal that corresponds to rotational displacement between the two elongated members.

45. The apparatus of claim 44, further comprising a linear capstan that couples the first actuator to the second elongated member.

46. The apparatus of claim 44, further comprising a cable drive and rotary bearing that couples the second actuator to the first elongated member.

* * * * *